(12) United States Patent
Kawahara et al.

(10) Patent No.: US 7,678,925 B2
(45) Date of Patent: Mar. 16, 2010

(54) PROCESSES OF PRODUCING GLUTAMIC ACID COMPOUNDS AND PRODUCTION INTERMEDIATES THEREFORE AND NOVEL INTERMEDIATE FOR THE PROCESSES

(75) Inventors: Shigeru Kawahara, Kawasaki (JP); Nao Funakoshi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/951,395

(22) Filed: Dec. 6, 2007

(65) Prior Publication Data

US 2008/0091032 A1 Apr. 17, 2008

Related U.S. Application Data

(60) Division of application No. 11/283,943, filed on Nov. 22, 2005, now Pat. No. 7,390,909, which is a division of application No. 10/872,573, filed on Jun. 22, 2004, now Pat. No. 7,064,219, which is a continuation of application No. PCT/JP02/12473, filed on Nov. 29, 2002.

(30) Foreign Application Priority Data

| Dec. 27, 2001 | (JP) | ............................... 2001-396300 |
| May 23, 2002 | (JP) | ............................... 2002-149069 |
| May 23, 2002 | (JP) | ............................... 2002-149078 |
| Jun. 21, 2002 | (JP) | ............................... 2002-182032 |

(51) Int. Cl.
*C07D 209/18* (2006.01)

(52) U.S. Cl. .................................................... 548/495
(58) Field of Classification Search .................. 548/495
See application file for complete search history.

(56) References Cited

U.S. PATENT DOCUMENTS

| 3,751,458 | A | 8/1973 | Wiley |
| 4,975,298 | A | 12/1990 | Van Wyk et al. |
| 5,128,482 | A | 7/1992 | Olivier et al. |
| 5,994,559 | A | 11/1999 | Abushanab et al. |
| 7,064,219 | B2 | 6/2006 | Kawahara et al. |
| 7,351,569 | B2 * | 4/2008 | Sugiyama et al. ........... 435/232 |
| 7,572,607 | B2 | 8/2009 | Hicks et al. |
| 2004/0063175 | A1 | 4/2004 | Abraham et al. |
| 2005/0244937 | A1 | 11/2005 | Abraham et al. |
| 2005/0282260 | A1 | 12/2005 | Hicks et al. |
| 2006/0074249 | A1 | 4/2006 | Kawahara et al. |
| 2008/0091032 | A1 | 4/2008 | Kawahara et al. |
| 2008/0274518 | A1 | 11/2008 | Hicks et al. |
| 2009/0117625 | A1 | 5/2009 | Abraham et al. |

FOREIGN PATENT DOCUMENTS

| EP | 0 438 314 | 7/1991 |
| JP | 64-025757 | 1/1989 |
| JP | 04-217654 | 8/1992 |
| WO | WO 03/059865 | 7/2003 |
| WO | 03/091396 | 11/2003 |
| WO | WO 03/091396 A2 | 11/2003 |

OTHER PUBLICATIONS

Abraham et al., 2003, CAS: 139:36397.*
K. Juhl, et al., "Catalytic Asymmetric Homo-Aldol Reaction of Pyruvate-A Chiral Lewis Acid Catalyst That Mimies Aldolase Enzymes", Chemical Communications, 2000, No. 22, pp. 2211-2212.
G. Buldain, et al., "Carbon-13 Nuclear Magnetic Resonance Spectra of the Hydrate, ETO and ENOL Forms of Oxalacetic Acid", Magnetic Resonance in Chemistry, 1985, vol. 23, No. 6, pp. 478-481.
D. Oliveira, et al., "Diastereoselective Formation of a Quaternary Center in a Pyroglutamate Derivative. Formal Synthesis of Monatain", Tetrahedron Letters, vol. 42, 2001, pp. 6793-6796.
K. Nakamura, et al., "Total Synthesis of Monatin", Organic Letters, vol. 2, No. 19, 2000, pp. 2967-2970.
C. Holzapfel, "A Simple Cycloaddition Approach to a Racemate of the Natural Sweetener Monatin", Synthetic Communications, vol. 24, No. 22, 1994, pp. 3197-3211.
C. Holzapfel, "The Synthesis of a γ-Keto-α-Amino Acid, A Key Intermediate in the Synthesis of Monatin, A New Natural Sweetener", Synthetic Communications, vol. 23, No. 18, 1993, pp. 2511-2526.
T. Kitahara, et al., Japanese Agrochemical Association, the 2000$^{th}$ Conference, Abstracts of Proceeding, 3B128β, p. 221.
R. Wiley, et al., "The Bimolecular Decarboxylative Self-Condensation of Oxaloacetic Acid to Citroylformic Acid and Its Conversion by Oxidative Decarboxylation to Citric Acid", J. Org. Chem., vol. 38, No. 20, 1973, pp. 3582-3585.
D. Lessing, et al., "A Nuclear Magnetic Resonance Study of Aqueous Pyruvate-Glycinate-Zinc(II) and Related Systems", Journal of American Chemical Society, vol. 86, Jul. 20, 1964, pp. 2805-2810.
S. Margolis, et al., "Identification and Quantitatior of the Impurities in Sodium Pyruvate", Analytical Chemistry, vol. 58, No. 12, 1986, pp. 2504-2510.
N. Passerate, et al., "Large Scale Enzymatic Synthesis of Diastereoisomeric γ-Hydroxy L-Glutamic Acids", Tetrahedron Letters, vol. 28, No. 12, 1987, pp. 1277-1280.
U.S. Appl. No. 12/028,360, filed Feb. 8, 2008, Kawahara et al.
Kozo Nakamura et al., "Total Synthesis of Monatin", Organic Letters, vol. 2, No. 19, p. 2967-2970 (2000).
Cedric W. Holzapfel., "A Simple Cycloaddition Approach To A Racemate Of The Natural Sweetener Monatin", Synthetic Communications, vol. 24, No. 22, p. 3197-3211 (1994).
105,696, Jun. 25, 2009, Kawahara et al.

* cited by examiner

*Primary Examiner*—Rei-tsang Shiao
(74) *Attorney, Agent, or Firm*—Oblon, Spivak, McClelland, Maier & Neustadt, L.L.P.

(57) ABSTRACT

The present invention relates to processes of producing glutamic acid compounds, for example, monatin, which are useful as, for example, production intermediates for sweetener or pharmaceutical products.

2 Claims, No Drawings

US 7,678,925 B2

PROCESSES OF PRODUCING GLUTAMIC ACID COMPOUNDS AND PRODUCTION INTERMEDIATES THEREFORE AND NOVEL INTERMEDIATE FOR THE PROCESSES

CONTINUING APPLICATION INFORMATION

This application is a Divisional of U.S. application Ser. No. 11/283,943, filed on Nov. 22, 2005, now pending, which is a Divisional of U.S. application Ser. No. 10/872,573, filed on Jun. 22, 2004, now U.S. Pat. No. 7,064,219, which is a Continuation of international application No PCT/JP02/12473, filed on Nov. 29, 2002.

BACKGROUND OF THE INVENTION

1. Field of the Invention

The present invention relates to processes of producing glutamic acid compounds such as monatin, useful as production intermediates for sweetener or pharmaceutical products, as well as production intermediates therefore, and a novel important intermediate included in them. More specifically, the invention relates to a process of industrially efficiently producing the glutamic acid compounds, a process of producing production intermediates for use therefore and a novel intermediate included in them, and a process of producing optically active monatin, a process of producing production intermediates for use therefore, including a novel intermediate.

2. Description of the Background

Glutamic acid compounds such as monatin are compounds that are promising for use as sweetener or production intermediates for pharmaceutical products and the like. For example, it has been known that 4-hydroxy-4-(3-indolylmethyl)-2-aminoglutaric acid (3-(1-amino-1,3-dicarboxy-3-hydroxybutan-4-yl)indole, sometimes referred to as "monatin" hereinbelow) represented by the following formula (7') in the (2S,4S) form is contained in the root of a plant *Schlerochiton ilicifolius* and has sweetness at a level several hundreds-fold that of sucrose (see JP-A-64-25757 (U.S. Pat. No. 4,975,298)).

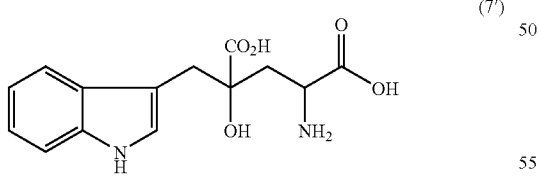

(7')

In the specification, the term "monatin" is not limited to the (2S,4S) form naturally occurring but is used as the generic name of 4-hydroxy-4-(3-indolylmethyl)-2-aminoglutaric acid (3-(1-amino-1,3-dicarboxy-3-hydroxybutan-4-yl)indole) including the individual isomers in the forms of (2S,4S), (2S,4R), (2R,4S), and (2R,4R).

The following reports have been issued about processes of producing monatin (the following examples (2) to (5)) and protected monatin (the following example (1)).

(1) Process described in Tetrahedron Letters, 2001, Vol. 42, No. 39, pp. 6793-6796;

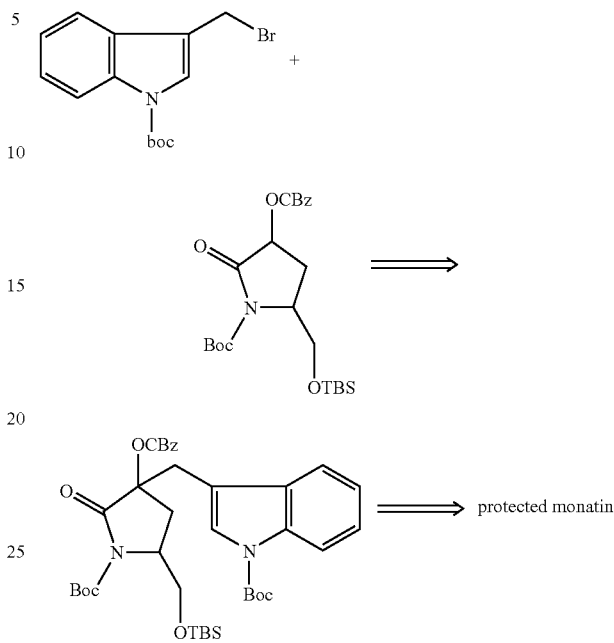

(2) Process described in Organic Letters, 2000, Vol. 2, No. 19, pp. 2967-2970;

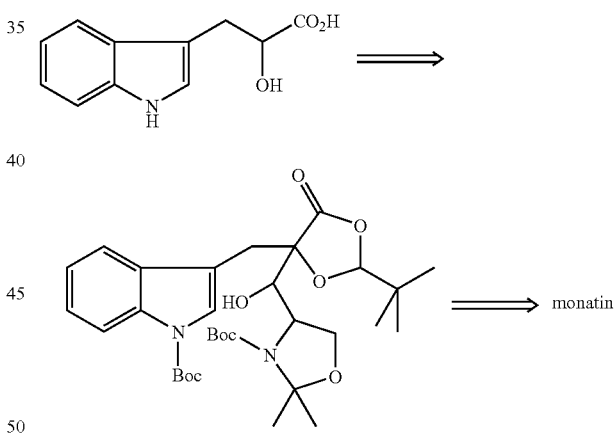

(3) Process described in U.S. Pat. No. 5,994,559;

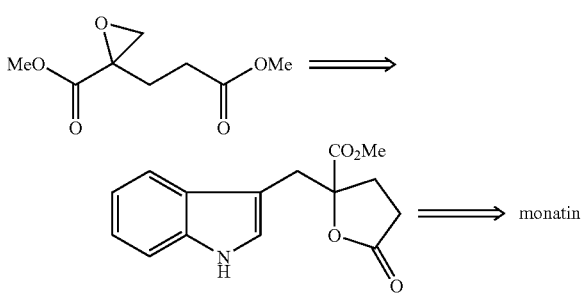

(4) Process described in Synthetic Communications, 1994, Vol. 24, No. 22, pp. 3197-3211;

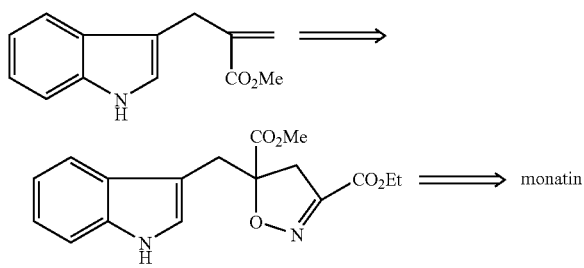

and
(5) Process described in Synthetic Communications, 1993, Vol. 23, No. 18, pp. 2511-2526 and U.S. Pat. No. 4,975,298 and U.S. Pat. No. 5,128,164;

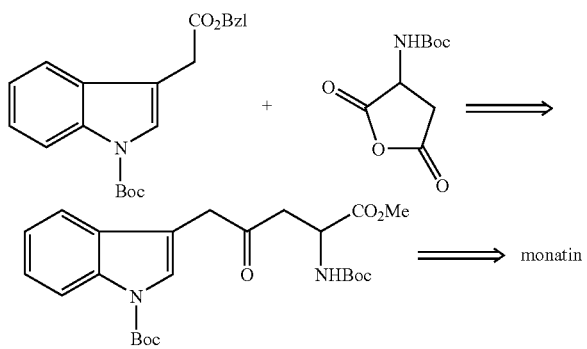

Because any of the processes requires multiple steps, however, the industrial practice of the processes actually involves much difficulty. Some of the references shown above or other references (see T. Kitahara, et al., Japanese Agrochemical Association, the 2000-th Conference, Abstracts of Proceedings, 3B128β (p. 221)) describe about the examination of processes of producing optically active monatin. However, disadvantageously, the processes require multiple steps and involve very tough steps for industrial practice. Thus, it has been desired to develop an industrial process of efficiently producing glutamic acid compounds typically including monatin, particularly an industrial process of efficiently producing optically active monatin.

SUMMARY OF THE INVENTION

The problems to be solved by the present invention are to provide processes of industrially and efficiently producing glutamic acid compounds such as monatin and production intermediates therefore (including salt forms of them) and to provide important intermediates therefore. More specifically, the invention provides a process of industrially efficiently producing the glutamic acid compounds, a process of producing production intermediates for use therefore and a novel important intermediate included in them, and a process of producing optically active monatin, a process of producing production intermediates for use therefore and a novel important intermediate included in them.

The inventors have made investigations so as to solve the problems described above. The inventors have found that glutamic acid compounds such as monatin (including salt forms thereof) can be efficiently produced by condensing a specific pyruvic acid compound and oxalacetic acid or pyruvic acid together with cross aldol reaction to produce ketoglutaric acid compounds as precursors of the intended glutamic acid compounds and then converting the carbonyl group in the resulting ketoglutaric acid compounds to amino group.

In an aldol reaction using carbonyl compounds of different types as in the present invention, generally, four types of products are produced in mixture through the self aldol reaction of the same types of compounds and the cross aldol reaction of different types of compounds. Although the self aldol condensation reaction of oxalacetic acid (Journal of Organic Chemistry, 1973, Vol. 38, No. 20, pp. 3582-3585) or pyruvic acid (Journal of American Chemical Society, 1964, Vol. 86, pp. 2805-2810; Analytical Chemistry, 1986, Vol. 58, No. 12, pp. 2504-2510) or the cross aldol reaction in a system where one of carbonyl compounds such as glyoxylic acid or oxalacetic acid is never condensed with itself so a single product can relatively readily be obtained (Tetrahedron Letters, 1987, Vol. 28, pp. 1277-1280) has been known so far, no report has described any example of selectively obtaining a single cross aldol reaction product between oxalacetic acid or pyruvic acid and pyruvic acid compounds.

Additionally, the inventors have found that an optically active monatin can be obtained by reacting a glutaric acid compound of the following formula (9) with a specific optically active amine to form a diasteromer salt, then crystallizing and separating the resulting diastereomer salt, further dissociating the diastereomer salt or exchanging the diastereomer salt with a different salt to obtain an optically active glutaric acid compound, then converting the alkoxyimino group (or hydroxyimino group) of the diastereomer salt or the optically active glutaric acid compound to amino group, crystallizing the resulting monatin represented by the following formula (13) (racemate at the 2-position) in a mixed solvent of water and an organic solvent.

Based on their findings described above, the invention has been achieved.

Thus, the invention includes inventions relating to the following production processes described below and the novel substance described below in their individual various embodiments.

A process of producing a glutamic acid compound represented by the following formula (7) or a salt thereof, including a step of treating a pyruvic acid compound represented by the following formula (1) and oxalacetic acid represented by the following formula (2) by cross aldol reaction and decarboxylation reaction or treating the pyruvic acid compound (except for pyruvic acid) and a pyruvic acid represented by the following formula (2') by cross aldol reaction, to obtain a ketoglutaric acid compound represented by the following formula (4) or a salt thereof, and a step of converting the carbonyl group of the ketoglutaric acid compound or a salt thereof to amino group, where the pyruvic acid compound, oxalacetic acid and pyruvic acid may individually be in salt forms thereof:

-continued

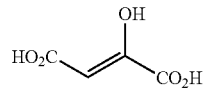
(2)

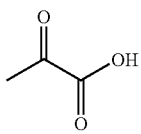
(2')

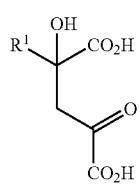
(4)

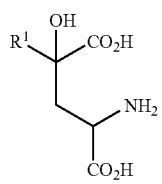
(7)

in the above formulas, $R^1$ represents a group selected from alkyl groups, aryl groups, aralkyl groups and heterocyclic ring-containing hydrocarbon groups; and $R^1$ may have at least one substituent selected from halogen atoms, hydroxyl group, alkyl groups with one to 3 carbon atoms, alkoxy groups with one to 3 carbon atoms and amino group.

A process described above in where the step of converting the carbonyl group of the ketoglutaric acid compound represented by the formula (4) or a salt thereof to amino group includes a step of reacting an amine compound represented by the following formula (5) or a salt thereof with the ketoglutaric acid or a salt thereof, to obtain a glutaric acid compound represented by the following formula (6) or a salt thereof, and a step of treating the resulting glutaric acid compound or a salt thereof by reducing reaction:

NH$_2$OR$^2$ (5)

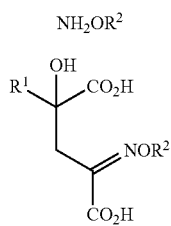
(6)

in the above formulas, $R^1$ represents a group selected from alkyl groups, aryl groups, aralkyl groups and heterocyclic ring-containing hydrocarbon groups; $R^2$ represents hydrogen atom or a group selected from alkyl groups, aryl groups and aralkyl groups; and $R^1$ may have at least one substituent selected from halogen atoms, hydroxyl group, alkyl groups with one to 3 carbon atoms, alkoxy groups with one to 3 carbon atoms and amino group.

A process described above in where the step of converting the carbonyl group of the ketoglutaric acid represented by the formula (4) or a salt thereof to amino group includes a step of treating the ketoglutaric acid compound or a salt thereof by reductive animation reaction.

A process described above where the cross aldol reaction is carried out within a range of pH 10 to 14.

A process of producing a ketoglutaric acid compound represented by the following formula (4) or a salt thereof, including a step of treating a pyruvic acid compound represented by the following formula (1) and oxalacetic acid represented by the following formula (2) by cross aldol reaction and decarboxylation reaction, or treating the pyruvic acid compound (except for pyruvic acid) and a pyruvic acid represented by the following formula (2') by cross aldol reaction, where the pyruvic acid compound, oxalacetic acid and pyruvic acid may individually be in salt forms thereof:

$$R^1 \underset{O}{\underset{\|}{\text{—}}} CO_2H \qquad (1)$$

$$HO_2C \underset{}{\overset{OH}{\text{—}}} CO_2H \qquad (2)$$

$$\underset{O}{\overset{O}{\text{—}}} \underset{}{\overset{}{\text{—}}} OH \qquad (2')$$

$$R^1 \underset{}{\overset{OH}{\text{—}}} CO_2H \qquad (4)$$
$$\phantom{R^1}\underset{CO_2H}{\overset{O}{\text{—}}}$$

in the above formulas, $R^1$ represents a group selected from alkyl groups, aryl groups, aralkyl groups and heterocyclic ring-containing hydrocarbon groups; and $R^1$ may have at least one substituent selected from halogen atoms, hydroxyl group, alkyl groups with one to 3 carbon atoms, alkoxy groups with one to 3 carbon atoms and amino group.

A process described above where the cross aldol reaction is conducted within a range of pH 10 to 14.

A process of producing a glutamic acid compound represented by the following formula (7) or a salt thereof, including a step of reacting a ketoglutaric acid compound represented by the following formula (4) or a salt thereof with an amine compound represented by the following formula (5) or a salt thereof, to obtain a glutaric acid compound represented by the following formula (6) or a salt thereof, and a step of treating the resulting glutaric acid compound or a salt thereof by reducing reaction:

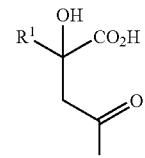  (4)

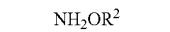  (5)

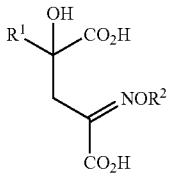  (6)

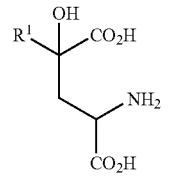  (7)

in the above formulas, R¹ represents a group selected from alkyl groups, aryl groups, aralkyl groups and heterocyclic ring-containing hydrocarbon groups; R² represents hydrogen atom or a group selected from alkyl groups, aryl groups and aralkyl groups; and R¹ may have at least one substituent selected from halogen atoms, hydroxyl group, alkyl groups with one to 3 carbon atoms, alkoxy groups with one to 3 carbon atoms and amino group.

A process of producing a glutamic acid compound represented by the following formula (7) or a salt thereof, including a step of treating a ketoglutaric acid compound represented by the following formula (4) or a salt thereof by reductive amination reaction:

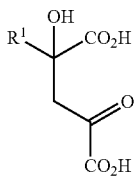  (4)

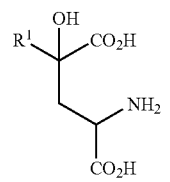  (7)

in the above formulas, R¹ represents a group selected from alkyl groups, aryl groups, aralkyl groups and heterocyclic ring-containing hydrocarbon groups; and R¹ may have at least one substituent selected from halogen atoms, hydroxyl group, alkyl groups with one to 3 carbon atoms, alkoxy groups with one to 3 carbon atoms and amino group.

A process of producing monatin represented by the following formula (7') or a salt thereof, including a step of treating indole-3-pyruvic acid represented by the following formula (1') and oxalacetic acid represented by the following formula (2) by cross aldol reaction and decarboxylation reaction, or treating indole-3-pyruvic acid represented by the following formula (1') and pyruvic acid represented by the following formula (2') by cross aldol reaction, to obtain 4-hydroxy-4-(3-indolylmethyl)-2-ketoglutaric acid represented by the following formula (4') or a salt thereof, and a step of converting the carbonyl group of the ketoglutaric acid or a salt thereof to amino group, where indole-3-pyruvic acid, oxalacetic acid and pyruvic acid may individually be in salt forms thereof:

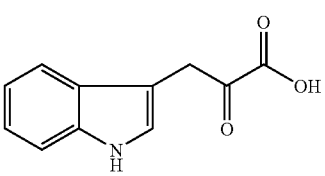  (1')

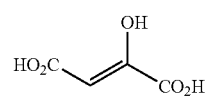  (2)

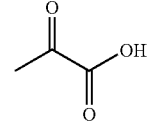  (2')

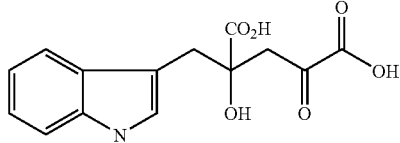  (4')

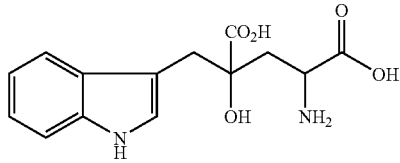  (7')

A process described above where the step of converting the carbonyl group of 4-hydroxy-4-(3-indolylmethyl)-2-ketoglutaric acid represented by the formula (4') or a salt thereof to amino group includes a step of reacting an amine compound represented by the following formula (5) or a salt thereof with the ketoglutaric acid or a salt thereof to obtain a glutaric acid compound represented by the following formula (6') or a salt thereof, and a step of treating the glutaric acid compound or a salt thereof by reducing reaction:

NH₂OR²  (5)

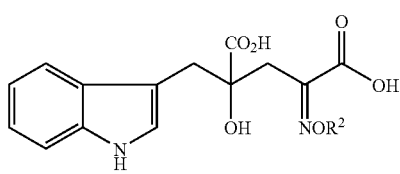  (6')

in the formula, $R^2$ represents hydrogen atom, or a substituent selected from alkyl groups, aryl groups and aralkyl groups.

A process described above where the step of converting the carbonyl group of 4-hydroxy-4-(3-indolylmethyl)-2-ketoglutaric acid represented by the formula (4') or a salt thereof to amino group includes a step of treating the ketoglutaric acid compound or a salt thereof by reductive amination reaction.

A process described above where the cross aldol reaction is carried out within a range of pH 10 to 14.

A process of producing 4-hydroxy-4-(3-indolylmethyl)-2-ketoglutaric acid represented by the following formula (4') or a salt thereof, including a step of treating indole-3-pyruvic acid represented by the following formula (1') and oxalacetic acid represented by the following formula (2) by cross aldol reaction and decarboxylation reaction, or treating indole-3-pyruvic acid represented by the following formula (1') and pyruvic acid represented by the following formula (2') by cross aldol reaction, where indole-3-pyruvic acid, oxalacetic acid and pyruvic acid may individually be in salt forms thereof:

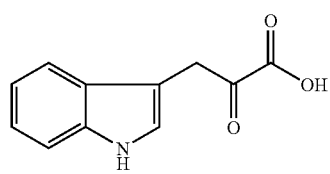
(1')

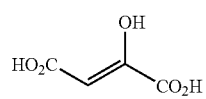
(2)

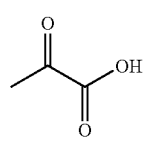
(2')

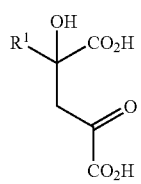
(4)

A process described above where the cross aldol reaction is carried out within a range of pH 10 to 14.

A process of producing monatin represented by the following formula (7') or a salt thereof, including a step of reacting 4-hydroxy-4-(3-indolylmethy)-2-ketogluraric acid represented by the following formula (4') or a salt thereof with an amine compound represented by the following formula (5) or a salt thereof, to obtain a glutaric acid compound represented by the following formula (6') or a salt thereof, and a step of subsequently treating the glutaric acid compound or a salt thereof by reducing reaction:

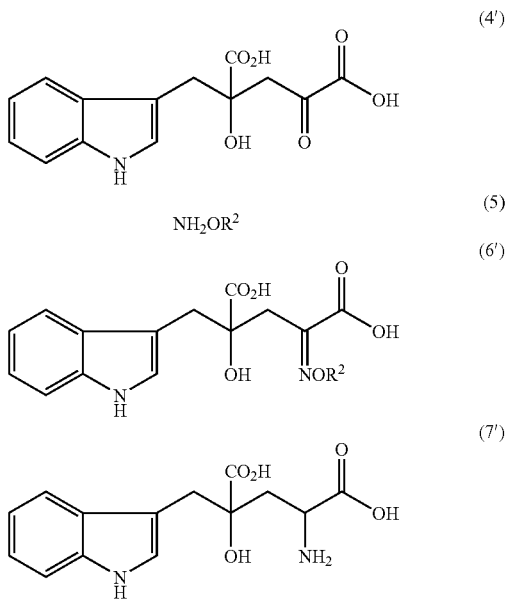

(4')

(5) $NH_2OR^2$ (6')

(7')

in the formula, $R^2$ represents hydrogen atom and a substituent selected from alkyl groups, aryl groups and aralkyl groups.

A process of producing monatin represented by the following formula (7') or a salt thereof, including a step of treating 4-hydroxy-4-(3-indolylmethyl)-2-ketoglutaric acid represented by the following formula (4') or a salt thereof by reductive amination reaction:

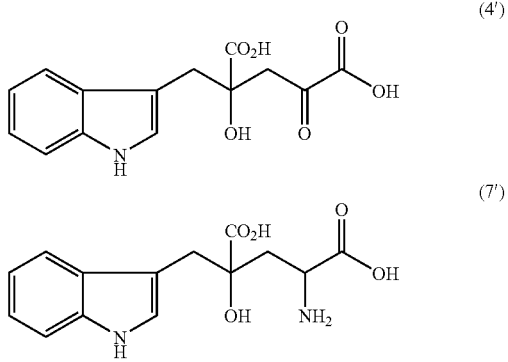

(4')

(7')

A process of producing an optically active monatin represented by the following formula (8) or a salt thereof, including the following steps a to c:

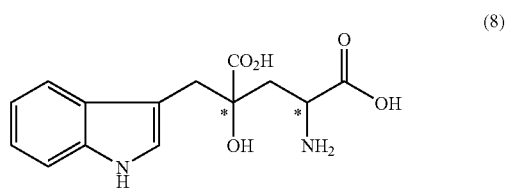
(8)

in the formula, * denotes an asymmetric center and independently represents the R- or S-configuration:

step a: a step of obtaining an optically active glutaric acid compound salt represented by the following formula (11)

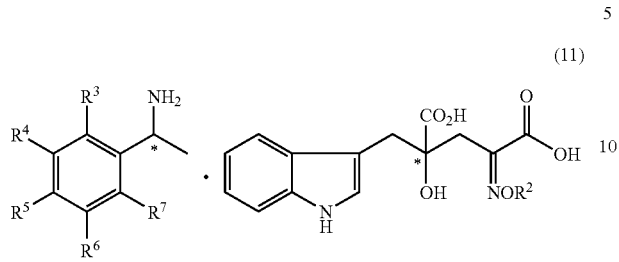
(11)

in the formula, $R^2$, $R^3$, $R^4$, $R^5$, $R^6$ and $R^7$ represent the same meanings as described below; in the formula, * denotes an asymmetric center and independently represents R- or S-configuration by reacting a glutaric acid compound represented by the following formula (9)

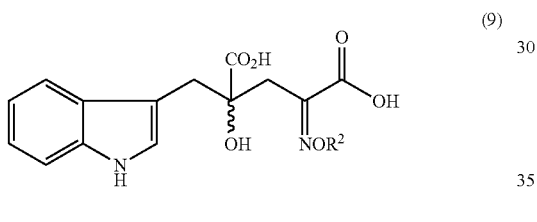
(9)

in the formula, $R^2$ represents hydrogen atom, an alkyl group, an aryl group or an aralkyl group; and the bond marked with wavy line expresses that both the R-configuration and the S-configuration are included with an optically active amine represented by the following formula (10)

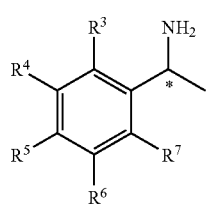
(10)

in the formula, $R^3$, $R^4$, $R^5$, $R^6$ and $R^7$ independently represent hydrogen atom or an alkyl group with one to 3 carbon atoms; * denotes an asymmetric center and represents R-configuration or S-configuration, to form a diastereomer salt, and a step of separating the diastereomer salt by crystallization;

step b: a step of generating monatin represented by the following formula (13) or a salt thereof

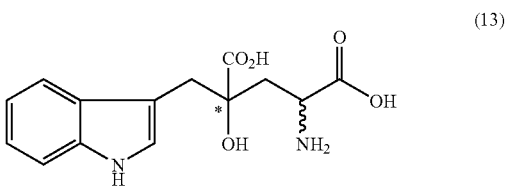
(13)

in the formula, * denotes an asymmetric center and represents R- or S-configuration; and the bond marked with wavy line means that both the R-configuration and the S-configuration are included, by dissociating the optically active glutaric acid compound salt represented by the formula (11) or exchanging the optically active glutaric acid compound salt with a different salt, as necessary, to prepare an optically active glutaric acid compound represented by the following formula (12) or a salt thereof (excluding the optically active glutaric acid compound salt represented by the formula (11))

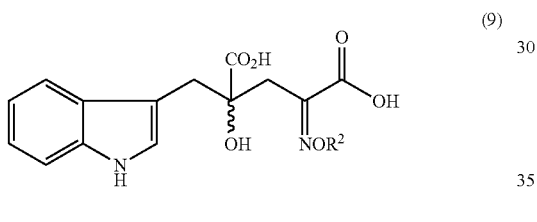
(12)

in the formula, $R^2$ represents hydrogen atom, an alkyl group, an aryl group or an aralkyl group; in the formula, * denotes an asymmetric center and represents the R-configuration or the S-configuration, and a step of converting the alkoxyimino group or hydroxyimino group to amino group;

step c: a step of obtaining an optically active monatin represented by the formula (8) or a salt thereof by crystallizing monatin represented by the formula (13) or a salt thereof using a mixed solvent of water and an organic solvent.

A process of producing an optically active monatin represented by the following formula (8) or a salt thereof, including the following steps b and c:

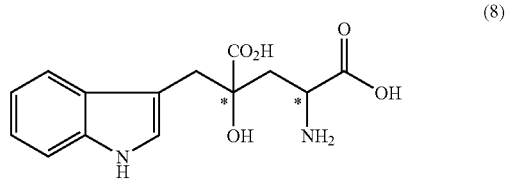
(8)

in the formula, * denotes an asymmetric center and independently represents the R- or S-configuration step b: a step of generating monatin represented by the following formula (13) or a salt thereof

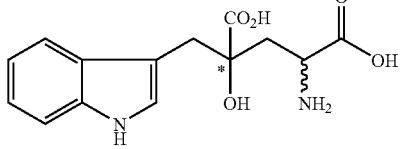
(13)

in the formula, * denotes an asymmetric center and represents R- or S-configuration; and the bond marked with wavy line means that both the R-configuration and the S-configuration are included, by dissociating an optically active glutaric acid compound salt represented by the following formula (11)

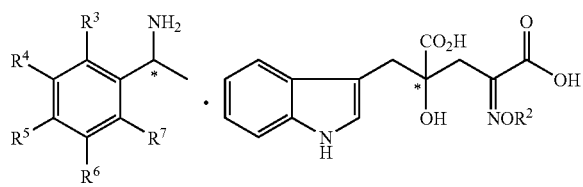
(11)

in the formula, $R^2$ represents hydrogen atom, an alkyl group, an aryl group or an aralkyl group; $R^3$, $R^4$, $R^5$, $R^6$ and $R^7$ independently represent hydrogen atom or an alkyl group with one to 3 carbon atoms; and * denotes an asymmetric center and independently represents the R- or S-configuration or exchanging the optically active glutaric acid compound salt with a different salt, as necessary, to prepare an optically active glutaric acid compound represented by the following formula (12) or a salt thereof (excluding the optically active glutaric acid compound salt represented by the formula (11))

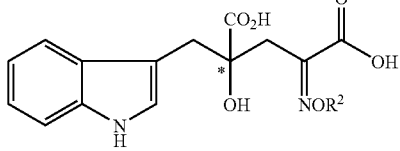
(12)

in the formula, $R^2$ represents hydrogen atom, an alkyl group, an aryl group or an aralkyl group; and * denotes an asymmetric center and represents the R-configuration or the S-configuration, and by treating the optically active glutaric acid compound by a reaction to convert the alkoxyimino group or hydroxyimino group thereof to amino group and step c: a step of obtaining an optically active monatin represented by the formula (8) or a salt thereof by crystallizing the monatin represented by the formula (13) or a salt thereof using a mixed solvent of water and an alcohol.

A process of producing an optically active monatin represented by the following formula (8) or a salt thereof

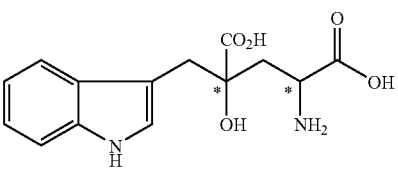
(8)

in the formula, * denotes an asymmetric center and independently represents the R- or S-configuration, including a step of crystallizing the salt of monatin represented by the following formula (13) using a mixed solvent of water and alcohol:

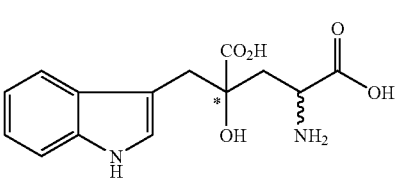
(13)

in the formula, * denotes an asymmetric center and represents R- or S-configuration; and the bond marked with wavy line means both the R-configuration and the S-configuration are included.

A process of producing an optically active glutaric acid compound salt represented by the following formula (11)

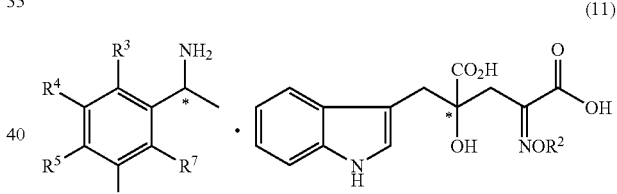
(11)

in the formula, $R^2$ represents hydrogen atom, an alkyl group, an aryl group or an aralkyl group; $R^3$, $R^4$, $R^5$, $R^6$ and $R^7$ independently represent hydrogen atom or an alkyl group with one to 3 carbon atoms; and * denotes an asymmetric center and independently represents the R- or S-configuration, including a step of reacting a glutaric acid compound represented by the following formula (9)

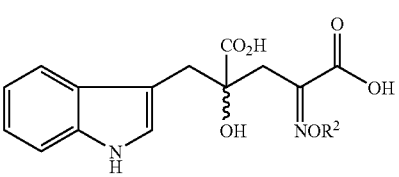
(9)

in the formula, $R^2$ represents hydrogen atom, an alkyl group, an aryl group or an aralkyl group; and the bond marked with wavy line means that both the R-configuration and S-configuration are included with an optically active amine represented by the following formula (10)

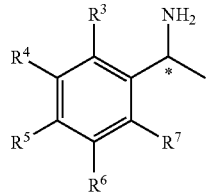
(10)

in the formula, $R^3$, $R^4$, $R^5$, $R^6$ and $R^7$ independently represent hydrogen atom or an alkyl group with one to 3 carbon atoms; * denotes an asymmetric center and represents the R- or S-configuration,
to form a diastereomer salt, and a step of separating the diastereomer salt by crystallization.

A process of producing an optically active glutaric acid compound represented by the following formula (12) or a salt thereof (excluding the optically active glutaric acid compound salt represented by the formula (11))

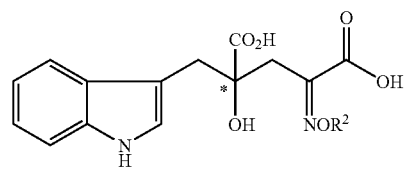
(12)

in the formula, $R^2$ represents hydrogen atom, an alkyl group, an aryl group or an aralkyl group; * denotes an asymmetric center and represents the R- or S-configuration,
including a step of dissociating an optically active glutaric acid compound salt represented by the following formula (11)

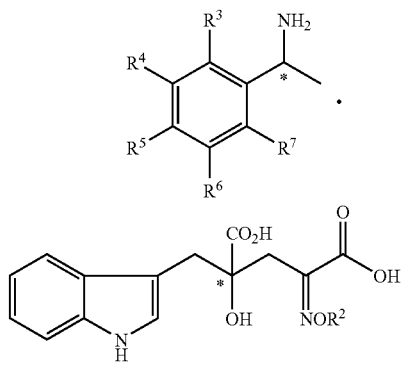
(11)

in the formula, $R^2$ represents hydrogen atom, an alkyl group, an aryl group or an aralkyl group; $R^3$, $R^4$, $R^5$, $R^6$ and $R^7$ independently represent hydrogen atom or an alkyl group with one to 3 carbon atoms; and * denotes an asymmetric center and independently represents the R- or S-configuration or exchanging the optically active glutaric acid compound salt with a different salt.

A process of producing monatin represented by the following formula (13) or a salt thereof:

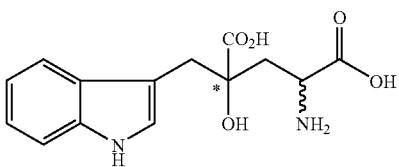
(13)

in the formula, * denotes an asymmetric center and represents the R- or S-configuration; the bond marked with wavy line expresses that both the R-configuration and the S-configuration are included,
including a step of dissociating an optically active glutaric acid compound salt represented by the following formula (11)

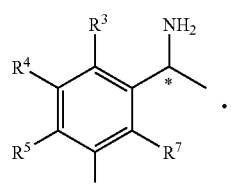
(11)

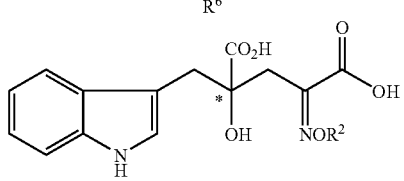

in the formula, $R^2$ represents hydrogen atom, an alkyl group, an aryl group or an aralkyl group; $R^3$, $R^4$, $R^5$, $R^6$ and $R^7$ independently represent hydrogen atom or an alkyl group with one to 3 carbon atoms; and * denotes an asymmetric center and independently represents the R- or S-configuration or exchanging the optically active glutaric acid compound salt with a different salt on a needed basis, to prepare an optically active glutaric acid compound represented by the following formula (12) or a salt thereof (excluding the optically active glutaric acid compound salt represented by the formula (11))

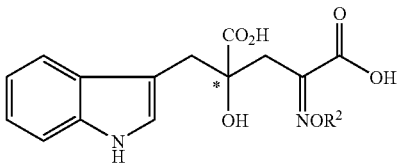
(12)

in the formula, $R^2$ represents hydrogen atom, an alkyl group, an aryl group or an aralkyl group; * denotes an asymmetric center and represents the R-configuration or the S-configuration and a step of treating the resulting optically active glutaric acid compound by a reaction to convert the alkoxyimino group or hydroxyimino group thereof to amino group.

A process of producing monatin represented by the following structural formula (7') (including salt forms thereof), the process passing through a process described above:

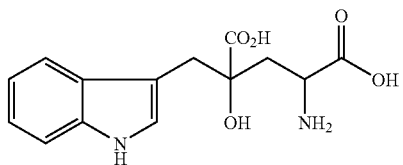
(7')

A compound represented by the following formulas or the formula (4'), (6'), (7"), (11), (12), (14), (15), (16) or (17) (including salt forms thereof), where in the formulas, $R^2$ represents hydrogen atom, an alkyl group, an aryl group or an aralkyl group; $R^3$, $R^4$, $R^5$, $R^6$ and $R^7$ independently represent hydrogen atom or an alkyl group with one to 3 carbon atoms; and * denotes an asymmetric center and represents the R- or S-configuration:

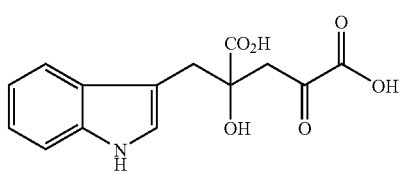
(4')

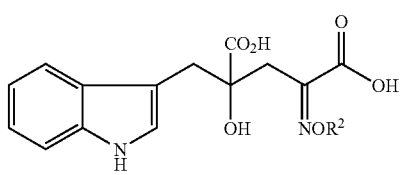
(6')

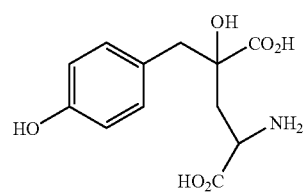
(7")

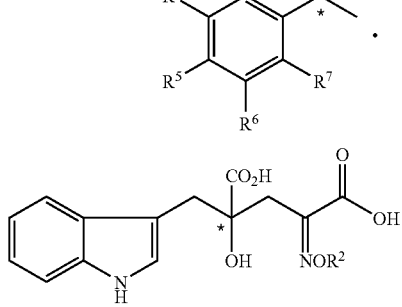
(11)

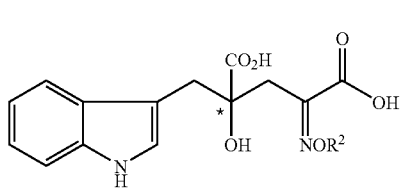
(12)

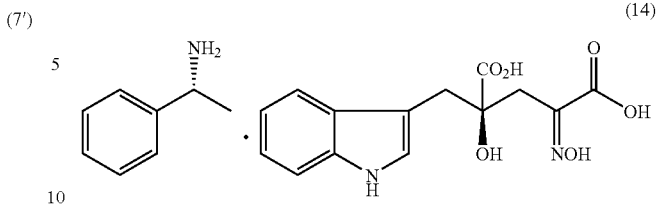
(14)

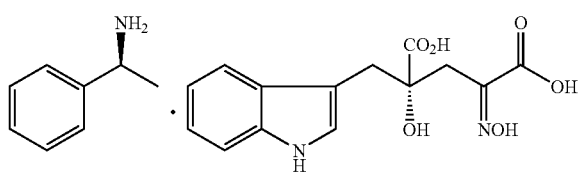
(15)

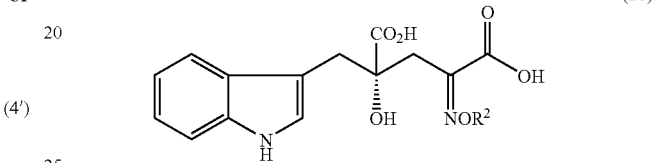
(16)

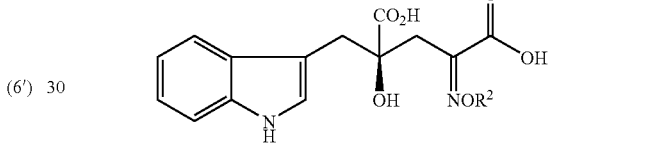
(17)

In an embodiment that such a compound is used or prepared in an appropriate salt form in accordance with the invention, the salt form is with no specific limitation. Such salt form includes for example sodium salt, potassium salt, lithium salt, magnesium salt, calcium salt, ammonium salt, and dicyclohexylammonium salt. By salt formation process, desalting process, salt exchange process and the like for routine use so far, the intended salt can be produced.

DETAILED DESCRIPTION OF THE INVENTION

The more-detailed procedures for carrying out the invention is now described below.

Production of ketoglutaric acid compound by cross aldol reaction and decarboxylation reaction between pyruvic acid compound and oxalacetic acid and derivative preparation as glutamic acid compound.

The pyruvic acid compound represented by the following formula (1) and oxalacetic acid represented by the following formula (2) are treated by cross aldol reaction and decarboxylation reaction or the pyruvic acid compound (excluding pyruvic acid) and pyruvic acid represented by the following formula (2') are treated by cross aldol reaction, to obtain a ketoglutaric acid compound represented by the following formula (4) or a salt thereof, and then, the carbonyl group of the ketoglutaric acid compound or a salt thereof is converted to amino group, to produce a glutamic acid compound represented by the following formula (7) or a salt thereof. In this case, the pyruvic acid compound, oxalacetic acid and pyruvic acid may individually be in salt forms.

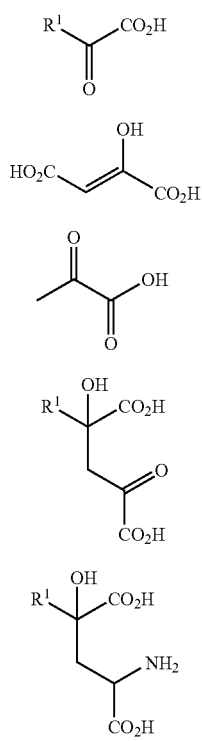

In the formulas, $R^1$ represents a group selected from alkyl groups, aryl groups, aralkyl groups and heterocyclic ring-containing hydrocarbon groups. These groups may have at least one substituent selected from halogen atoms (iodine atom, bromine atom, chlorine atom, fluorine atom, etc.), hydroxyl group, alkyl groups with one to 3 carbon atoms, alkoxy groups with one to 3 carbon atoms and amino group.

As $R^1$, alkyl groups, aryl groups, aralkyl groups and heterocyclic ring-containing hydrocarbon groups with one to 11 carbon atoms (never including the carbon number in substituents if these groups contain the substituents) are preferable. For example, $R^1$ includes alkyl groups such as isopropyl group, isobutyl group and 1-methylpropyl group, aryl groups such as phenyl group and 3-indolyl group, aralkyl groups such as benzyl group, 2-phenylethyl group and 2-naphthylmethyl group and heterocyclic ring-containing hydrocarbon groups such as 3-indolylmethyl group and 3-(6-methylindolyl)methyl group.

For the aldol reaction between the pyruvic acid compound represented by the formula (1) and the pyruvic acid represented by the formula (2'), herein, the case that the pyruvic acid compound represented by the formula (1) is pyruvic acid, namely the case that $R^1$ is methyl group (the alkyl group with one carbon atom) is never included.

Examples of $R^1$ with substituents include $R^1$ having an aromatic ring or heterocyclic ring, provided that the aromatic ring or heterocyclic ring contains at least one substituent selected from alkyl groups with one to 3 carbon atoms, alkoxy groups with one to 3 carbon atoms, and amino groups. When a benzyl group or 3-indolylmethyl group for example is selected as $R^1$ in the formula, specifically, the benzene ring or indole ring contained in the group may contain at least one substituent selected from halogen atoms (iodine atom, bromine atom, chlorine atom, fluorine atom, etc.), hydroxyl group, alkyl groups with one to 3 carbon atoms, alkoxy groups with one to 3 carbon atoms, and amino group.

In an embodiment where $R^1$ is 3-indolylmethyl group, in other words, in case that indole-3-pyruvic acid (formula 1') is used as the pyruvic acid compound, 4-hydroxy-4-(3-indolylmethyl)-2-ketoglutaric acid (formula 4') or a salt thereof as an intermediate important for monatin production can be obtained. Subsequently by converting the carbonyl group of the ketoglutaric acid or a salt thereof to amino group, monatin (formula 7') or a salt thereof can be produced.

Cross Aldol Reaction

The cross aldol reaction is preferably carried out under alkaline conditions. The pyruvic acid compound and oxalacetic acid, or the pyruvic acid compound (excluding pyruvic acid) and pyruvic acid may be present in an appropriate solvent for the reaction.

As the reaction solvent, polar solvents such as water, methanol, ethanol, propanol, acetonitrile and dimethylformamide or mixed solvents thereof are preferable. Particularly, water and a mixed solvent (hydrous organic solvent) of water and polar solvents are preferable.

The pH of the solvent is within a range of preferably 10 to 14, more preferably 10.5 to 14, still more preferably 11 to 13. When the pH is too high, the yield is likely to decrease. When the pH is too low, secondary reactions are likely to take place during the cross aldol reaction.

Bases may satisfactorily be used to achieve such pH under alkaline conditions, and include, for example, inorganic bases such as alkali metal salts and alkali earth metal salts including alkali earth metal hydroxides and carbonates, e.g., lithium hydroxide, sodium hydroxide, potassium hydroxide, sodium carbonate, potassium carbonate and calcium carbonate, and organic bases such as triethylamine.

The amount of oxalacetic acid or pyruvic acid to be used to the amount of the pyruvic acid compound has no specific limitation. When oxalacetic acid or pyruvic acid is used in excess, the reaction yield is likely to be improved. Generally, one to 10 equivalents of oxalacetic acid or pyruvic acid are used to one equivalent of the pyruvic acid compound. Preferably, pyruvic acid can be used within a range of 3 to 6 equivalents.

The reaction can be carried at a reaction temperature within a range of preferably −10 to 70° C., more preferably 10 to 50° C. When the reaction temperature is too low, the intended reaction progresses so slowly that secondary reactions are likely to occur. When the reaction temperature is high, the intended ketoglutaric acid compound (or a salt thereof) is likely to be decomposed.

The reaction time has no specific limitation, and is generally one to 72 hours, preferably 3 to 24 hours.

Decarboxylation Reaction

The reaction with oxalacetic acid is then progressed to decarboxylation reaction, to subsequently obtain the intended ketoglutaric acid compound (or a salt thereof). The reaction for decarboxylating the condensate from the aldol reaction between oxalacetic acid and the pyruvic acid compound can be achieved by spontaneous decarboxylation reaction. However, the decarboxylation reaction can be effectively progressed by adding an acid or a metal ion or both to the reaction solution. The acid for use then includes for example hydrochloric acid, sulfuric acid, phosphoric acid, acetic acid, p-toluenesulfonic acid, solid acids such as ion exchange resins, while the metal ion includes for example transition metal ions such as nickel ion, copper ion, and iron ion. As the reaction temperature, preferably about −10 to 100° C., more preferably about 0 to 60° C. can be selected.

The reaction solution after the cross aldol reaction or after the cross aldol reaction and decarboxylation reaction may satisfactorily be used for the subsequent step as it is. From the reaction solution the ketoglutaric acid compound (or a salt thereof) represented by the formula (4) is isolated and purified, for use in the subsequent step. When the subsequent amination step is continuously carried out, generally, the ketoglutaric acid compound (or a salt thereof) need not be isolated. After the completion of the reaction, the reaction solution is concentrated or distilled off, if necessary, for the amination step. By using the same solvent as used in the cross aldol reaction step for the amination step, the following step can be carried out with no distillation or solvent substitution of reaction solvent or the like. In case that the ketoglutaric acid compound represented by the formula (4) is obtained as a salt, the salt is prepared in a free form by a method known to a person skilled in the art, for use in the amination step. However, generally, it is not necessary to do so. The salt can be used in its salt form.

In the cross aldol reaction (and decarboxylation reaction if necessary) in accordance with the invention where $R^1$ is 3-indolylmethyl group, i.e. where indole-3-pyruvic acid (formula 1') is used as the pyruvic acid compound, 4-hydroxy-4-(3-indolylmethyl)-2-ketogluratic acid (formula 4'), as an intermediate important for monatin production, or a salt thereof can be produced.

Conversion of the Carbonyl Group to an Amino Group

After the cross aldol reaction is carried out (and subsequently the decarboxylation reaction is carried out if necessary), the carbonyl group of the ketoglutaric acid compound represented by the formula (4) or a salt thereof is converted to amino group, to produce a glutamic acid compound represented by the formula (7). The reaction to convert carbonyl group to amino group is with no specific limitation and is carried out for example by the following methods.

Conversion Example 1 of a Carbonyl Group to an Amino Group

After the cross aldol reaction is carried out (and subsequently the decarboxylation reaction is carried out if necessary), an amine compound (which may be in a salt form) represented by the following formula (5) is reacted with the ketoglutaric acid compound represented by the formula (4) or a salt thereof, to produce a glutaric acid compound represented by the formula (6) or a salt thereof, which is then treated by reducing reaction to produce a glutamic acid compound represented by the formula (7).

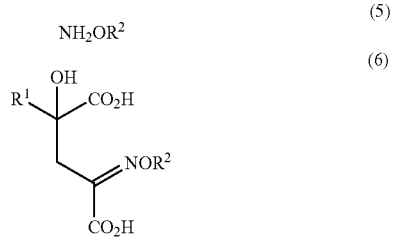

In the formula, $R^1$ is as described above.

In the case where $R^1$ is a 3-indolylmethyl group, i.e. in case that 4-hydroxy-4-(3-indolylmethyl)-2-ketogluratic acid (formula 4') is used as the ketoglutaric acid represented by the formula (4) or a salt thereof, herein, a glutaric acid compound represented by the formula (6') or a salt thereof is once produced, which is then treated by reduction reaction to produce monatin represented by the formula (7') or a salt thereof.

In the formula, $R^2$ represents a hydrogen atom or a group selected from alkyl groups, aryl groups and aralkyl groups and the like. $R^2$ is preferably selected from hydrogen atom and alkyl groups and aralkyl groups with 7 or less carbon atoms.

Specifically, $R^2$ is preferably a hydrogen atom, methyl group or benzyl group, particularly preferably hydrogen atom. In other words, specific examples of the amine compound represented by the formula (5) preferably include hydroxylamine, methoxyamine and benzyloxyamine, particularly preferably include hydroxylamine.

The salt of the amine compound represented by the formula (5) includes salt forms of the amine compound with organic acids or inorganic acids and specifically includes for example hydroxylamine hydrochloride salt, hydroxylamine sulfate salt and methoxyamine hydrochloride salt.

In case that hydroxylamine hydrochloride reacts with 4-hydroxy-4-(3-indolylmethyl)-2-ketogluratic acid represented by the formula (4'), for example, the corresponding 4-hydroxy-4-(3-indolylmethyl)-2-hydroxyiminogluratic acid (the compound of formula (6') where $R^2$ is hydrogen atom) is obtained in good yield.

For the reaction of the ketoglutaric acid compound represented by the formula (4) or a salt thereof with the amine compound represented by the formula (5) or a salt thereof, the reaction temperature can be set at preferably about −10 to 100° C., more preferably about 0 to 60° C. Further, the reaction time can be set at preferably about one to 100 hours, more preferably about 1 to 24 hours.

For the reaction of the amine compound or a salt thereof, the pH of the reaction solution is preferably 2 or more because the reaction progresses slowly when the pH is too low. The reaction can be progressed more preferably at about pH 2 to 13, still more preferably at about pH 4 to 12.

The ratio of the amine compound or a salt thereof to be used is with not particularly limited. However, the amine compound (or a salt thereof) is used preferably at about one to 7 moles, more preferably at about one to 2 moles per one mole of the ketoglutaric acid compound (or a salt thereof) represented by the formula (4).

As the reaction solvent, polar solvents such as water, methanol, ethanol, propanol, acetonitrile and dimethylformamide, or mixed solvents thereof are preferable. Particularly, water and a mixed solvent of water with polar solvents (hydrous organic solvents) are preferable.

As thus obtained, the reaction solution thus obtained, containing the glutaric acid compound (or a salt thereof) represented by the formula (6), may satisfactorily be used as it is for the subsequent step. Otherwise, the glutaric acid compound may be isolated and purified from the reaction solution, prior to use in the next step.

When the isolation and purification is carried out, methods known to a person skilled in the art such as extraction and crystallization can appropriately be used. For example, the glutaric acid compound represented by the formula (6') may be obtained as follows. That is, by acidifying the reaction solution by adjusting the pH of the reaction solution with acids such as hydrochloric acid, extracting the glutaric acid compound in organic solvents such as ethyl acetate, concentrating the resulting organic layer and crystallizing the residue in a mixed solvent of aqueous ammonia and alcohol, the glutaric acid compound represented by the formula (6') can be obtained as the diammonium salt thereof in crystals. Using ion exchange resins or adsorption resins or the like, the compound in the free form can be isolated from the reaction solution. The glutaric acid compound represented by the formula (6') or a salt thereof as obtained in such manner is generally a racemate, from which the optically active form can be obtained by a method described below.

Then, the glutaric acid compound represented by the formula (6) (or a salt thereof) is treated by reduction reaction, to produce a glutamic acid compound represented by the following formula (7). Through the reaction, the alkoxyimino group (or hydroxyimino group) at the 2-position in the glutaric acid compound represented by the formula (6) can be converted to amino group.

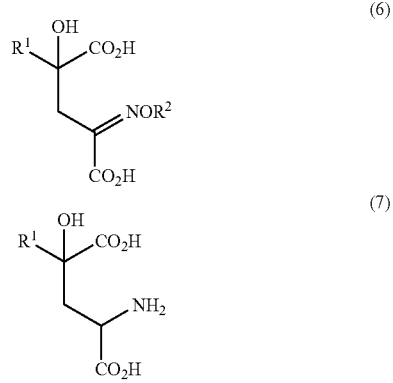

In the formulas, $R^1$ and $R^2$ are as described above.

The reduction of the alkoxyimino group (or hydroxyimino group) to amino group can preferably be carried out by hydrogenation reaction using a catalyst for hydrogenation.

As the catalyst for hydrogenation, there can be used palladium-type catalysts (palladium carbon, etc.), platinum-type catalysts (platinum carbon, etc.), rhodium-type catalysts (rhodium carbon, etc.), ruthenium-type catalysts (ruthenium carbon, etc.), nickel-type catalysts (Raney-nickel, etc.) and the like.

These catalysts are used within a range of preferably 0.1 to 20 mol %, more preferably 0.5 mol % to 5 mol % of the substrate.

As the reaction solvent, polar solvents such as water, methanol, ethanol, propanol, acetonitrile and dimethylformamide or mixed solvents thereof are preferable. Particularly, water and a mixed solvent (hydrous organic solvent) of water with polar solvents are preferable.

The reaction of this step is preferably carried out under alkaline conditions, generally within a range of pH 7 to 14, preferably within a range of pH 8 to 12. In the case of using rhodium-type catalysts (rhodium carbon, etc.), in particular, the reaction is carried out generally within a range of pH 7.5 to 11, preferably within a range of pH 8 to 10. In the case of using nickel-type catalysts (Raney nickel, etc.), however, the reaction preferably progresses under neutral conditions, generally within a range of pH 5 to 9, preferably within a range of pH 6.5 to 7.5. If pH is too high, the reaction of this step is likely to give rise to an increase of by-products. If pH is too low, the reaction is likely to progress slowly. In case that the reaction is carried out under alkaline conditions, the type of an alkali for use in pH adjustment is not specifically limited. For the reduction reaction using rhodium-type catalysts and palladium-type catalysts, especially, aqueous ammonia is preferably used for the reaction, because of the increase of the yield and low by-products.

The hydrogenation reaction is preferably carried out in a hydrogen atmosphere. As the hydrogen pressure, a range of preferably 0.5 to 100 atmospheres, more preferably 3 to 70 atmospheres, is desirable for the reaction.

The reaction temperature is within a range of preferably −20 to 100° C., more preferably 0 to 70° C. The reaction time can be 6 to 24 hours.

Conversion Example 2 of the Carbonyl Group to an Amino Group

By converting the carbonyl group at the 2-position in the ketoglutaric acid compound represented by the following formula (4) (or a salt thereof) by reductive amination reaction using amines such as ammonia, benzylamine and 1-phenylethylamine, a glutamic acid compound represented by the following formula (7) can be obtained.

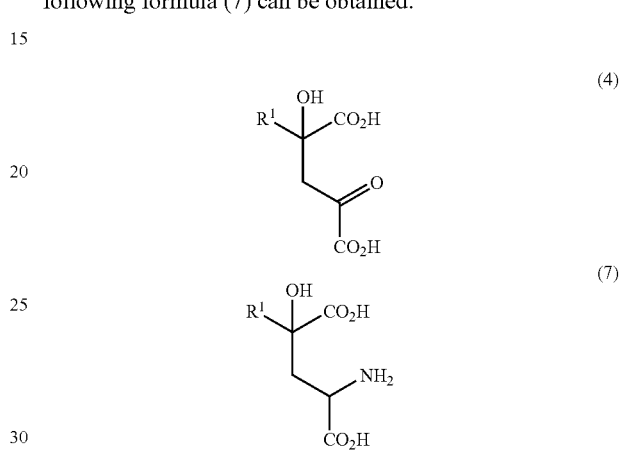

In the formulas, $R^1$ is as described above.

In case that $R^1$ is 3-indolylmethyl group, i.e. in case that 4-hydroxy-4-(3-indolylmethyl)-2-ketogluratic acid (formula 4') is used as the ketoglutaric acid compound represented by the formula (4) or a salt thereof, herein, monatin represented by the formula (7') or a salt thereof can be produced.

Amine can be used within a range of preferably one to 10 equivalents to the ketoglutaric acid compound (or a salt thereof). When ammonia is to be used as the amine, herein, a large excess of ammonia is preferably used.

As the reducing catalyst, hydride catalysts such as $NaBH_4$ in addition to the hydrogenation catalysts described above can be used. In the case of a hydride catalyst, the catalyst can be used at an amount generally within a range of 0.5 to 2 equivalents. In the case of a hydrogenation catalyst, the catalyst at an amount similar to the amount used for contact hydrogenation of the glutaric acid compound represented by the formula (6) can be used. The reaction can preferably be progressed at a reaction temperature within a range of preferably 0 to 50° C., more preferably 20 to 35° C. The reaction time is within a range of preferably 1 to 72 hours. In case of using a catalyst for hydrogenation, the reaction can be carried out at a hydrogen pressure within 1 to 15 atmospheric pressures.

As the reaction solvent, polar solvents such as water, methanol, ethanol, propanol, acetonitrile and dimethylformamide or mixed solvents thereof are preferable. Particularly, water and a mixed solvent (hydrous organic solvent) of water with polar solvents are preferable.

The glutaric acid compound (or a salt thereof) represented by the formula (7) as obtained by the processes in the two examples can be isolated and purified, using methods known to a person skilled in the art, such as extraction and crystallization. In case that $R^1$ is 3-indolylmethyl group, i.e. in case that 4-hydroxy-4-(3-indolylmethyl)-2-ketogluratic acid (formula 4') is used as the ketoglutaric acid compound represented by the formula (4) or a salt thereof, herein, monatin represented by the formula (7') or a salt thereof can be produced. Monatin represented by the formula (7') or a salt thereof can be isolated and purified by a method for producing optically active monatin as described below, to obtain the optically active form.

Production of Optically Active Monatin

Monatin has asymmetric carbon atoms at the 2- and 4-positions, so the following four types of optical isomers exist.

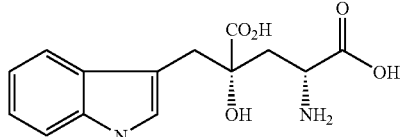

(2R, 4R) form

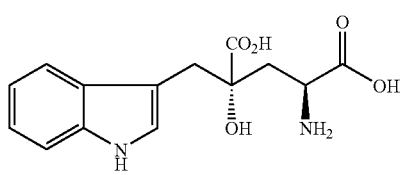

(2S, 4R) form

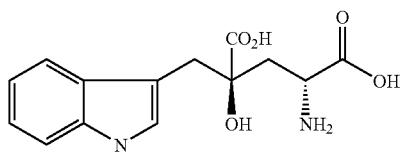

(2R, 4S) form

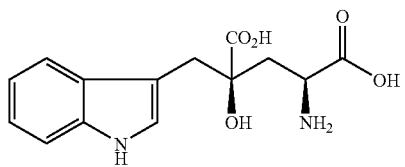

(2S, 4S) form

In case that 4-hydroxy-4-(3-indolylmethyl)-2-ketogluratic acid (formula 4') is used as the ketoglutaric acid compound represented by the formula (4) or a salt thereof as described above, reaction with an amine compound represented by the formula (5) or a reagent generating the compound can produce the glutaric acid compound represented by the formula (6') or a salt thereof, which is generally a racemate.

The racemate or the glutaric acid compound containing the R-form and S-form at an appropriate ratio (these are included in the glutaric acid compound represented by the formula (9)) is treated by the following steps a to c, to obtain optically active forms of monatin or a salt thereof.

step a: a step of obtaining an optically active glutaric acid compound salt represented by the following formula (11)

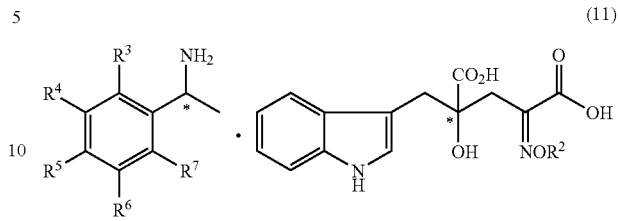

(11)

in the formula, $R^2$, $R^3$, $R^4$, $R^5$, $R^6$ and $R^7$ represent the same meanings as described below; and * denotes an asymmetric center and independently represents R- or S-configuration, by reacting a glutaric acid compound represented by the following formula (9)

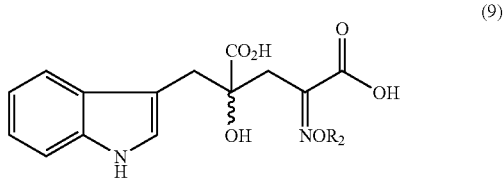

(9)

in the formula, $R^2$ represents hydrogen atom, an alkyl group, an aryl group or an aralkyl group; and the bond marked with wavy line expresses that both the R-configuration and the S-configuration are included with an optically active amine represented by the following formula (10)

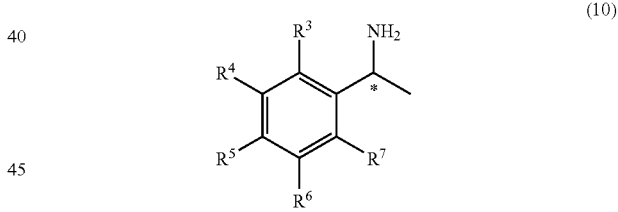

(10)

in the formula, $R^3$, $R^4$, $R^5$, $R^6$ and $R^7$ independently represent hydrogen atom or an alkyl group with one to 3 carbon atoms; and * denotes an asymmetric center and represents R-configuration or S-configuration, to form a diastereomer salt and then separating the diastereomer salt by crystallization;

step b: a step of generating monatin represented by the following formula (13) or a salt thereof

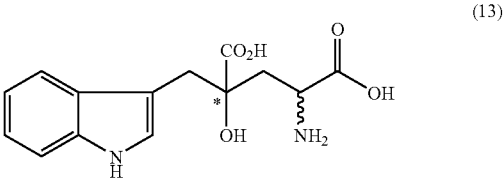

(13)

in the formula, * denotes an asymmetric center and represents R- or S-configuration; and the bond marked with wave line means that both the R-configuration and the S-configuration are included, by dissociating the optically active glutaric acid compound salt represented by the formula (11) or exchanging the optically active glutaric acid compound salt with a different salt, as necessary, to prepare an optically active glutaric acid compound represented by the following formula (12) or a salt thereof (excluding the optically active glutaric acid compound salt represented by the formula (11))

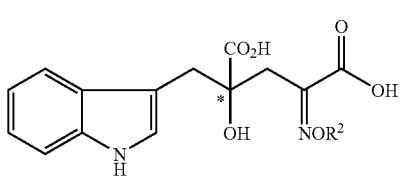
(12)

in the formula, $R^2$ represents hydrogen atom, an alkyl group, an aryl group or an aralkyl group; and * denotes an asymmetric center and represents the R-configuration or the S-configuration, and subsequently converting the alkoxyimino group or hydroxyimino group to amino group;

step c: a step of obtaining an optically active monatin represented by the formula (8) or a salt thereof by crystallizing monatin represented by the formula (13) or a salt thereof using a mixed solvent of water and an organic solvent.

Step a is described below.

So as to allow the glutaric acid compound represented by the formula (9) to form a diastereomer salt together with the optically active amine represented by the formula (10), for example, such compounds or salts thereof are dissolved in a solvent for the reaction. In case that the glutaric acid compound is in a salt form thereof, the salt is converted to the free form by neutralizing the salt with an acid as necessary and subsequently extracting the free form into an organic solvent, and then, the free form reacts with an optically active amine to form the salt. Additionally, an acid may satisfactorily be added to a solvent containing the glutaric acid compound salt dissolved therein to neutralize the salt, and then, an optically active amine may be added for the reaction to form the diastereomer salt. In case that the glutaric acid compound salt represented by the formula (11) is formed by a salt exchange reaction with an optically active amine represented by the formula (10) in a solvent, the salt form can even be used as is to react with the optically active amine represented by the formula (10). In this case, the optically active amine represented by the formula (10) is preferably used in a salt form such as hydrochloride salt or sulfate salt.

Particularly preferable examples of the optically active amine represented by the formula (10) include (R)-(+)-1-phenylethylamine and (S)-(−)-1-phenylethylamine, where $R^3$, $R^4$, $R^5$, $R^6$ and $R^7$ in the formula are hydrogen atoms.

The optically active amine is used at an amount of preferably about 0.1 to 1-fold mole, more preferably about 0.3 to 0.6-fold that of the glutaric acid compound.

The reaction temperature is set within a range of preferably about −20 to 100° C., more preferably about 0 to 60° C. The reaction time is not particularly limited but is short enough for rapid formation of the salt.

The reaction solvent includes a single solvent selected from water, methanol, ethanol, acetonitrile, toluene and ethyl acetate, and an appropriate mixed solvent of two or more thereof. Particularly, water or a mixed solvent of water and an organic solvent miscible with water (for example, polar solvents such as methanol, ethanol and acetonitrile) is preferably used. Of these, a single solvent of water is more preferable.

After the completion of the reaction, for example, the reaction solution is concentrated if necessary, and water is added to crystallize the diastereomer salt. The reaction solution may be cooled as necessary. Because water is a poor solvent for the resulting diastereomer salt, water or a mixed solvent of water with an organic solvent miscible with water is used as the reaction solvent for forming the diastereomer salt, so that the crystal can be deposited and crystallized, concurrently with the progress of the reaction (salt formation). The crystals obtained by crystallization are separated from the reaction solution by filtration and the like, to obtain the diastereomer salt represented by the formula (11). The diastereomer salt obtained as crystals in case of using water as the poor solvent varies depending on the steric configuration of the optically active amine used. In the case of using (R)-(+)-1-phenylethylamine as the optically active amine represented by the formula (10) for the 4-hydroxy-4-(3-indolylmethyl)-2-hydroxyiminoglutaric acid (a compound of the formula (9) where $R^2$ is hydrogen atom), for example, the diastereomer salt represented by the following formula (14) can be obtained. In the case of using (S)-(−)-1-phenylethylamine, the diastereomer salt represented by the following formula (15) can be obtained.

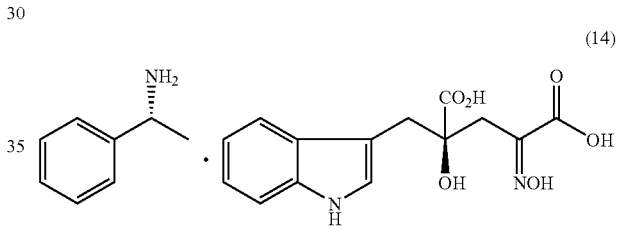
(14)

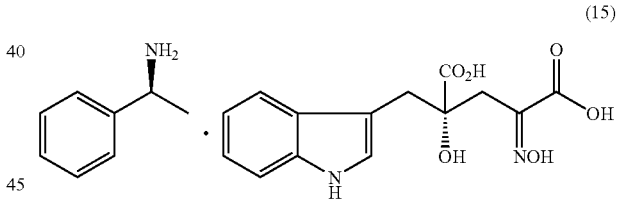
(15)

In the case of using (R)-(+)-1-phenylethylamine, in other words, a crystal of the diastereomer salt can be obtained, where the glutaric acid compound in the S-configuration at the 4-position forms the salt together with (R)-(+)-1-phenylethylamine. In the case of using (S)-(−)-1-phenylethylamine, a crystal of the diastereomer salt can be obtained, where the glutaric acid compound in the R-configuration at the 4-position forms the salt together with (S)-(−)-1-phenylethylamine. A person skilled in the art can select an optically active amine suitable for the intended compound, to form and crystallize such diastereomer salt, so that a diastereomer salt with a desired steric configuration can be obtained.

Further, after the separation of these diastereomer salts in crystals, the mother liquor contains a glutaric acid compound in a steric configuration opposite to the glutaric acid compound separated as crystals, as its main component. Thus, by adding an optically active amine with a steric configuration opposite to that of the optically active amine used to form the salt in the mother liquor, to form and crystallize the diastereomer salt in the same manner as described above, one additional diastereomer salt crystal can be separated from the mother liquor. In other words, the step a in accordance with the invention can be applied to the mother liquor to obtain another diastereomer salt by crystallization as described above.

Step b is described below.

The optically active glutaric acid compound salt represented by the formula (11) as obtained in the step a is dissociated to form an optically active glutaric acid compound represented by the formula (12), if necessary. Alternatively, the salt can be replaced by a different salt (salt exchange), if necessary.

In case of such dissociation and replacement with a different salt (salt exchange), methods known to a person skilled in the art can be used. The dissociation method is for example a method including a step of dissolving or suspending the salt in water, alcohol or a mixed solvent thereof, a step of neutralizing the resulting solution or suspension with acids such as hydrochloric acid or sulfuric acid, and an extraction step into organic solvents, a method including a step of dissolving the salt in water, and separating the free form represented by the formula (12) with ion exchange resins or adsorption resins. For isolation of the free form, the intended isolation can readily be carried out by a known method, for example distillation of a resin eluent solution, or of an extract solution containing the free form under reduced pressure. In case of the substitution with a different salt, for example, the optically active glutaric acid compound salt represented by the formula (11) can be dissolved in aqueous alkali metal solutions of sodium hydroxide and potassium hydroxide and aqueous ammonia solution, from which the free optically active amine is extracted in an organic solvent, so that the salt can be exchanged. Using a known method such as the distillation under reduced pressure of the aqueous solution after extraction or crystallization, additionally, the salt of the optically active glutaric acid compound represented by the formula (12) (excluding the optically active glutaric acid compound salt represented by the formula (11)) can be isolated.

Monatin represented by the formula (13) can be produced from the optically active glutaric acid compound represented by the formula (12) thus obtained or from a salt thereof by treating the alkoxyimino group (or hydroxyimino group) thereof with a reaction to convert the group to amino group. Further, monatin represented by the formula (13) can be produced by treating the alkoxyimino group (or hydroxyimino group) of the optically active glutaric acid compound salt represented by the formula (11) with a reaction to convert the group to amino group in the same manner as described above.

As described above, the conversion of the alkoxyimino group (or hydroxyimino group) to amino group can be carried out by hydrogenation reaction using a catalytic hydrogenation reagent, under reaction conditions as described above.

After the completion of the reaction, the catalyst is removed by filtration and the like and the filtrate is concentrated, if necessary, from which monatin represented by the formula (13) can be obtained by isolation methods known to a person skilled in the art (for example, crystallization, HPLC, etc.). In an embodiment where the next step c is to be continuously carried out, additionally, monatin represented by the formula (13) need not be isolated, in general. After the completion of the reaction, the catalyst is removed from the reaction solution by filtration and the like. Then, the reaction solution is concentrated or distilled off, if necessary, to carry out the crystallization according to the step c. By using the same solvent as used as the crystallization solvent for the hydrogenation reaction, the next step c can be carried out without distillation of the reaction solvent or solvent replacement or the like. In case that base is used for the hydrogenation reaction, monatin in the reaction solution exists in a salt form thereof. By treating the reaction solution after the removal of the catalyst with an ion exchange resin and the like, for example, monatin can be prepared as the free form or can be converted to a different salt (salt exchange including for example the conversion of ammonium salt to sodium salt or potassium salt or the like). Then, the resulting product can be crystallized. For carrying out the next step c, preferably, the resulting monatin is used in the salt form thereof as it is.

Step c is described below.

Although the monatin represented by the formula (13) or a salt thereof as obtained at the step b can retain the optical activity at the 4-position, the resulting monatin can be recovered as a mixture of the S form and R form at the 2-position. The monatin and a salt thereof can be optically resolved by crystallization according to the step c described next, so that optically active monatin or a salt thereof, optically active at both the 2- and 4-positions, can be obtained.

The monatin represented by the formula (13) or a salt thereof is treated by a crystallization step using a mixed solvent of water and an organic solvent, to obtain optically active monatin (crystal) represented by the formula (8).

In case that a base is used for the hydrogenation reaction at the step (b), generally, monatin can be obtained generally in a salt form thereof, which is preferably treated at a crystallization step, as it is in the salt form. In this case, water is a good solvent for the monatin salt. The crystallization method is not particularly limited, and includes for example methods known to a person skilled in the art, such as crystallization under cooling and concentration prior to crystallization. For crystallizing the monatin salt, for example, the monatin crystal in the free form can be obtained by adding an acid to an aqueous solution containing the monatin salt dissolved therein to neutralize the solution and by adding an organic solvent to the resulting solution. Because monatin is likely to be decomposed by an acid, however, the invention can preferably be used particularly in case that monatin is to be obtained in a salt form.

As the organic solvent, an organic solvent miscible with water can be used. Particularly, alcohols such as methanol, ethanol, propanol and isopropanol are preferable. A mixed solvent of different two types or more organic solvents may satisfactorily be used as the organic solvent. The ratio of an organic solvent and water in the mixed solvent with water may satisfactorily be set preferably within a range of an organic solvent:water=about 1:0.1 to 1:1 in volume ratio, more preferably within a range of an organic solvent:water=about 1:0.3 to 1:0.9 in volume ratio. The crystallization temperature may satisfactorily be set within a range of preferably about −20 to 100° C., more preferably about 0 to 60° C.

As shown below in the following schemes, the steric configuration of the monatin crystal obtained at the step c is as follows. In case of using monatin represented by the formula (13) in the R form at the 4-position and in the S form at the 4-position, the monatin crystals (2R,4R) and (2S,4S) are obtained, respectively. Additionally, the mother liquor after crystal separation individually contain (2S,4R) monatin and (2R,4S) monatin as the main component. By treating the mother solutions with adsorption resins and the like, (2S,4R) monatin or (2R,4S) monatin can be isolated.

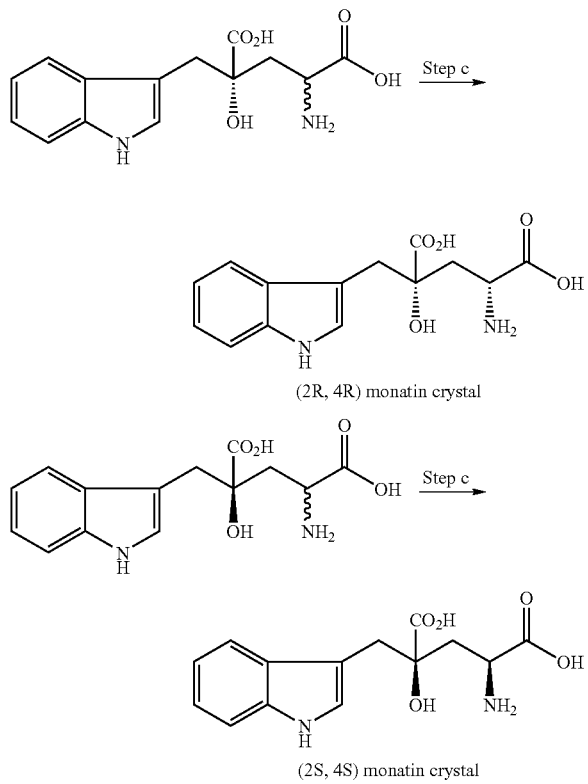

(2R, 4R) monatin crystal (2S, 4S) monatin crystal

If desired, the optically active monatin obtained in the free form can be prepared as a salt form. By methods known to a person skilled in the art (salt formation), the monatin can be prepared in salt forms, for example as a sodium salt or potassium salt. Further, even the optically active monatin obtained in a salt form thereof can be obtained similarly in the free form if desired or can be converted to a different salt. By utilizing methods known to a person skilled in the art, for example, the salt can be converted to the free form by a method for converting salts to free forms via dissociation and the like. Alternatively, the salt can be converted to the intended different salt by exchanging the resulting salt with a different salt (salt exchange).

EXAMPLES

The invention is now described in detail in the following Examples. However, the invention is not limited to the Examples.

In the Examples, further, the optical purity was assayed by HPLC under the following conditions.

Column for separating optical isomers
SUMICHIRAL OA-7100 manufactured by Sumika Chemical Analysis Service Eluent
20 mM phosphate buffer, pH 2.8: acetonitrile=7:3
Column temperature
10° C.; and
Flow rate
0.6 ml/min.

Example 1

Synthesis of 4-hydroxy-4-(3-indolylmethyl)-2-ketoglutaric acid; NO. 1

After 8.28 g of potassium hydroxide (having a purity of 85% by weight) was dissolved in 27 ml of water, 3.0 g (14.76 mmol) of indole-3-pyruvic acid and 5.85 g (44.29 mmol) of oxalacetic acid were added to the resulting solution, for reaction at ambient temperature for 72 hours (about pH 13 at the start of the reaction). An ion exchange resin (Amberlite IR 120B H AG) was added to the reaction solution to adjust the solution to pH 3.0, for extraction into 200 ml of ethyl acetate at 0° C. 100 ml of saturated aqueous sodium bicarbonate was added to the resulting ethyl acetate layer, and ethyl acetate in the ethyl acetate layer was distilled off, and pH of the solution was re-adjusted to 7.9 with an ion exchange resin (IRA400 OH AG manufactured by Organo Corporation). The resulting solution was freeze-dried as it was 4-Hydroxy-4-(3-indolylmethyl)-2-ketoglutarate sodium salt was obtained as a crude product. Further, 40 ml of water and 200 ml of ethanol were added to the resulting residue, in which the solid was filtered off. The resulting mother solution was concentrated to dryness, to obtain 4-hydroxy-4-(3-indolylmethyl)-2-ketoglutarate sodium salt of 1.5 g as a crude product.

Example 2

Synthesis of 4-hydroxy-4-(3-indolylmethyl)-2-ketoglutaric acid; NO. 2

After 18.91 g (286.5 mmol) of potassium hydroxide (at a content of 85% by weight) was dissolved in 64.45 ml of water, 7.50 g (35.8 mmol at a content of 97.0% by weight) of indole-3-pyruvic acid and 14.18 g (107.4 mmol) of oxalacetic acid were added to and dissolved in the resulting solution (about pH 13 at the start of the reaction). The mixed solution was stirred at 35° C. for 24 hours. Further, 40.0 ml of 3N hydrochloric acid was added for neutralization (pH=7.0), to obtain 153.5 g of a neutralized reaction solution. The neutralized reaction solution contained 5.55 g of 4-hydroxy-4-(3-indolylmethyl)-2-ketoglutaric acid at a yield of 53.5% (vs. indole-3-pyruvic acid). Water was added to the neutralized reaction solution to make up 168 ml, and the solution passed through a resin column (diameter of 4.8 cm) packed with a synthetic adsorbent (DIAION-SP207 manufactured by Mitsubishi Chemical Corporation) of 840 ml. Further, pure water was passed through the column at a flow rate of 23.5 ml per minute. 1.73 to 2.55 (L/L-R) were collected, to obtain an aqueous solution of 4-hydroxy-4-(3-indolylmethyl)-2-ketoglutaric acid of 3.04 g at a yield of 54.7% (to the charged amount in the resin).

(NMR Measurement)
$^1$H-NMR (400 MHz, $D_2O$): δ3.03 (d, 1H, J=14.6 Hz), 3.11 (d, 1H, J=14.6 Hz), 3.21 (d, 1H, J=18.1 Hz), 3.40 (d, 1H, J=18.1 Hz), 7.06-7.15 (m, 3H), 7.39 (d, 1H, J=7.8 Hz), 7.66 (d, 1H, J=7.8 Hz). $^{13}$C-NMR (400 MHz, $D_2O$): δ35.43, 47.91, 77.28, 109.49, 112.05, 119.44, 119.67, 121.91, 125.42, 128.41, 136.21, 169.78, 181.43, 203.58.

(Molecular Weight Measurement)

Theoretical ESI-MS value $C_{14}H_{13}NO_6$=291.07 Analytical value=290.02 (M-H)⁻.

Example 3

Synthesis of 4-hydroxy-4-(3-indolylmethyl)-2-ketoglutaric acid; NO. 3

After 3.70 g (56.0 mmol) of potassium hydroxide (at a content of 85% by weight) was dissolved in 72.1 ml of water, 0.81 g (4.0 mmol) of indole-3-pyruvic acid and 3.17 g (24.0 mmol) of oxalacetic acid were added to and dissolved in the resulting solution (about pH 13 at the start of the reaction). The mixed solution was stirred at 35° C. for 24 hours. A part of the reaction solution was treated with hydroxylamine to prepare 4-hydroxy-4-(3-indolylmethyl)-2-hydroxyiminoglutaric acid, which was analyzed by HPLC. Consequently, it was found that 4-hydroxy-4-(3-indolylmethyl)-2-ketoglutaric acid was generated at a yield of 76.6% (vs. indole-3-pyruvic acid).

Example 4

Synthesis of 4-benzyl-4-hydroxy-2-ketoglutaric acid

After 16.23 g of potassium hydroxide (having a purity of 85% by weight) was dissolved in 48 ml of water, 5.0 g (30.5 mmol) of phenylpyruvic acid and 12.1 g (91.4 mmol) of oxalacetic acid were added to the resulting solution, for reaction at ambient temperature for 72 hours (about pH 13 at the start of the reaction). Using conc. hydrochloric acid, the reaction solution was adjusted to pH 2.2, and extracted in ethyl acetate. The organic layer was rinsed in aqueous saturated sodium chloride, dried over anhydrous magnesium sulfate and concentrated to obtain the residue. The residue was recrystallized in ethyl acetate and toluene, to obtain 2.8 g (11.3 mmol) of 4-benzyl-4-hydroxy-2-ketoglutaric acid in crystal form.

(NMR Measurement)

$^1$H NMR (D$_2$O) δ: 2.48 (d, J=14.4 Hz, 0.18H), 2.60 (d, J=14.4 Hz, 0.18H), 2.85-3.30 (m, 3.64H), 7.17-7.36 (m, 5H).

(Molecular Weight Measurement)

Theoretical ESI-MS value $C_{12}H_{12}O_6$=252.23 Analytical value=251.22 (M-H)⁻.

Example 5

Synthesis of 4-hydroxy-4-(3-indolylmethyl)-2-hydroxyiminoglutaric acid; NO. 1

After 13.8 g of potassium hydroxide (having a purity of 85% by weight) was dissolved in 50 ml of water, 5.0 g (24.6 mmol) of indole-3-pyruvic acid and 9.8 g (73.8 mmol) of oxalacetic acid were added to the resulting solution, for reaction at ambient temperature for 72 hours (about pH 13 at the start of the reaction). To the reaction solution was added 6.8 g (98.4 mmol) of hydroxylamine hydrochloride salt. Then, the reaction solution was adjusted to pH 7.5 with aqueous 4N sodium hydroxide solution. After the reaction solution had been stirred for 24 hours at ambient temperature, the reaction solution was adjusted to pH 2.6 with 6N hydrochloric acid. After extraction using ethyl acetate, the organic layer was rinsed in aqueous saturated sodium chloride, dried over anhydrous magnesium sulfate and concentrated to dryness. The resulting residue was dissolved in 10 ml of aqueous 14% ammonia, followed by gradual dropwise addition of 70 ml of ethanol, and stirred at ambient temperature for 3 hours. The resulting slurry was filtered. The resulting crystals was dried to obtain 2.7 g (7.9 mmol) of 4-hydroxy-4-(3-indolylmethyl)-2-hydroxyiminoglutaric acid in the form of an ammonium salt.

(NMR Measurement)

$^1$H NMR (DMSO-d$_6$) δ: 2.66 (s, 2H), 2.89 (d, J=14.4 Hz, 1H), 3.04 (d, J=14.4 Hz, 1H), 6.89-6.94 (m, 1H), 6.97-7.03 (m, 1H), 7.11 (d, J=2.8 Hz, 1H), 7.27 (d, J=7.8 Hz, 1H), 7.53 (d, J=7.8 Hz, 1H), 10.71 (br s, 1H).

(Molecular Weight Measurement)

Theoretical ESI-MS value $C_{14}H_{14}N_2O_6$=306.28 Analytical value=305.17 (M-H)⁻.

Example 6

Synthesis of 4-hydroxy-4-(3-indolylmethyl)-2-methoxyiminoglutaric acid

After 9.12 g (138.1 mmol) of potassium hydroxide (at a content of 85% by weight) was dissolved in 23 ml of water, 2.55 g (12.2 mmol at a content of 97.0% by weight) of indole-3-pyruvic acid and 7.46 g (56.5 mmol) of oxaloacetic acid were added to and dissolved in the resulting solution (about pH 13 at the start of the reaction). The solution was stirred at 35° C. for 24 hours. To the reaction solution was gradually added 5.76 g (69 mmol) of methoxyamine hydrochloride salt while the reaction solution was adjusted to around pH 10 with aqueous 25% sodium hydroxide solution. After the reaction had continued at ambient temperature for 14 hours, the reaction solution was adjusted to pH 2.23, using 6N hydrochloric acid, and was then extracted in ethyl acetate. The organic layer was rinsed with aqueous saturated sodium chloride and dried over anhydrous magnesium sulfate. After the magnesium sulfate had been filtered off, the resulting solution was concentrated to obtain 4.66 g of residue. The resulting residue was approximately purified by silica gel column chromatography, and further coarsely purified by preparative thin layer chromatography (PTLC; ethyl acetate/hexane/acetic acid=5/5/1), to obtain 0.93 g of the title compound 4-hydroxy-4-(3-indolylmethyl)-2-methoxyiminoglutaric acid (2.92 mmol; yield, 24% (vs. indole-3-pyruvic acid)).

(NMR Measurement)

$^1$H-NMR (400 MHz, DMSO-d$_6$): δ2.89 (d, J=14.9 Hz, 1H), 3.04 (s, 2H), 3.15 (d, J=14.9 Hz, 1H), 3.90 (s, 3H), 6.91-6.96 (m, 1H), 6.98-7.04 (m, 1H), 7.09-7.12 (m, 1H), 7.29 (d, J=7.4 Hz, 1H), 7.50 (d, J=7.4 Hz, 1H), 10.80 (br s, 1H).

Example 7

Synthesis of 4-benzyl-4-hydroxy-2-hydroxyiminoglutaric acid

After 16.23 g (having a purity of 85% by weight) of potassium hydroxide was dissolved in 45 ml of water, 5.0 g (30.5 mmol) of phenylpyruvic acid and 12.1 g (91.4 mmol) of oxalacetic acid were added to the resulting solution, for reaction at ambient temperature for 24 hours (about pH 13 at the start of the reaction). To the reaction solution was added 8.5 g (121.8 mmol) of hydroxylamine hydrochloride salt, for reaction at ambient temperature for 72 hours. The reaction solution was adjusted to pH 2.6, using 6N hydrochloric acid, and was then extracted in ethyl acetate. The organic layer was rinsed with aqueous saturated sodium chloride, dried over anhydrous magnesium sulfate and concentrated to dryness. The resulting residue was recrystallized in 20 ml of ethyl acetate and 80 ml of toluene, to obtain 4.0 g (15.1 mmol) of 4-benzyl-4-hydroxy-2-hydroxyiminoglutaric acid.

(NMR Measurement)

$^1$H NMR (DMSO-$d_6$) δ: 2.80 (d, J=13.9 Hz, 1H), 2.99 (d, J=12.7 Hz, 1H), 3.01 (d, J=13.9 Hz, 1H), 3.03 (d, J=12.7 Hz, 1H), 7.13-7.25 (m, 5H).

(Molecular Weight Measurement)

Theoretical ESI-MS value $C_{12}H_{13}NO_6$=267.24 Analytical value=266.12 (M-H)$^-$.

Example 8

Synthesis of
4-hydroxy-4-(3-indolylmethyl)-2-aminoglutaric acid (monatin); NO. 1

0.13 g (0.38 mmol) of 4-hydroxy-4-(3-indolylmethyl)-2-hydroxyiminoglutaric acid ammonium salt was dissolved in 5 ml of aqueous 28% ammonia, to which 0.09 g of 5% rhodium carbon was added, for reaction at ambient temperature and a hydrogen pressure of 7.5 atmospheres. 14 hours later, the catalyst was filtered off, and the resulting solution was concentrated to dryness, to obtain a mixture of 0.075 g (0.23 mmol) of the ammonium salt of (2S,4S)/(2R,4R)-4-hydroxy-4-(3-indolylmethyl)-2-aminoglutaric acid (monatin) and 0.036 g (0.11 mmol) of the ammonium salt of (2S,4R)/(2R,4S)-4-hydroxy-4-(3-indolylmethyl)-2-aminoglutaric acid (monatin).

(NMR Measurement)

$^1$H NMR (D$_2$O) δ: 2.05 (dd, J=12.2, 15.1 Hz, 0.67H), 2.21 (dd, J=9.9, 15.6 Hz, 0.33H), 2.48 (dd, J=3.2, 15.6 Hz, 0.33H), 2.68 (dd, J=2.2, 15.1 Hz, 0.67H), 3.08 (d, J=14.4 Hz, 0.67H), 3.17-3.25 (m, 0.66H), 3.28 (d, J=14.4 Hz, 0.67H), 3.63 (dd, J=2.2, 12.2 Hz, 0.67H), 3.98 (dd, J=3.2, 9.9 Hz, 0.33H), 7.12-7.18 (m, 1H), 7.19-7.26 (m, 2H), 7.45-7.51 (m, 1H), 7.70-7.76 (m, 1H).

(Molecular Weight Measurement)

Theoretical ESI-MS value $C_{14}H_{16}N_2O_5$=292.29 Analytical value=291.28 (M-H)$^-$.

Example 9

Synthesis of
4-hydroxy-4-(3-indolylmethyl)-2-aminoglutaric acid (monatin); NO. 2

0.264 g (0.824 mmol) of 4-hydroxy-4-(3-indolylmethyl)-2-methoxyiminoglutaric acid was dissolved in 10 ml of aqueous 28% ammonia. 0.18 g of 5% rhodium carbon (dry product) was added and the mixture stirred at a hydrogen pressure of 7.5 atmospheres for 18 hours. The catalyst was filtered off and the solvent was distilled off under reduced pressure, to obtain the residue. The resulting residue was analyzed by NMR, and a mixture of 0.115 g (0.395 mmol; yield, 48%) of (2S,4S)/(2R,4R)-4-hydroxy-4-(3-indolylmethyl)-2-aminoglutaric acid (monatin) and 0.065 g (0.223 mmol; yield, 27%) of (2S,4R)/(2R,4S)-4-hydroxy-4-(3-indolylmethyl)-2-aminoglutaric acid was found to have been generated.

Example 10

Synthesis of
4-hydroxy-4-(3-indolylmethyl)-2-aminoglutaric acid (monatin); NO. 3

1.0 g (2.94 mmol) of 4-hydroxy-4-(3-indolylmethyl)-2-hydroxyiminoglutarate ammonium salt was dissolved in 10 ml of water, to which 1 ml of a Raney-nickel catalyst (manufactured by Kawaken Fine Chemicals Co., Ltd.; developed nickel catalyst NDHT-90) was added with a syringe, and the mixture stirred at a hydrogen pressure of 20 atmospheres for 10 hours. The catalyst was filtered off, and the resulting solution was concentrated to obtain the residue. The residue was analyzed by NMR. It was shown that 0.29 g (0.89 mmol; yield, 30%) of (2S,4S)/(2R,4R)-4-hydroxy-4-(3-indolylmethyl)-2-aminoglutaric acid (monatin) and 0.29 g (0.89 mmol; yield, 30%) of (2S,4R)/(2R,4S)-4-hydroxy-4-(3-indolylmethyl)-2-aminoglutaric acid were generated.

Example 11

Synthesis of 2-amino-4-benzyl-4-hydroxyglutaric acid; NO. 1

0.25 g (0.94 mmol) of 4-benzyl-4-hydroxy-2-hydroxyiminoglutaric acid was dissolved in 10 ml of aqueous 50% methanol solution, to which 0.5 ml of aqueous 28% ammonia was added. 1.0 g of 5% palladium-carbon (50% hydrous product) was added, for reaction at ambient temperature and a hydrogen pressure of 7.7 atmospheres. 72 hours later, the catalyst was filtered off, and the reaction solution was concentrated to dryness, to obtain 0.10 g (0.35 mmol) of the ammonium salt of (2S,4S)/(2R,4R)-2-amino-4-benzyl-4-hydroxyglutaric acid and 0.10 g (0.35 mmol) of the ammonium salt of (2R,4S)/(2S,4R)-2-amino-4-benzyl-4-hydroxyglutaric acid as a mixture.

(NMR Measurement)

$^1$H NMR (D$_2$O) δ: 1.94 (dd, J=11.9, 15.3 Hz, 0.5H), 2.10 (dd, J=10.2, 15.3 Hz, 0.5H), 2.36 (dd, J=3.1, 15.3 Hz, 0.5H), 2.56 (dd, J=2.4, 15.3 Hz, 0.5H), 2.81 (d, J=13.6 Hz, 0.5H), 2.94 (d, J=13.5 Hz, 0.5H), 3.01 (d, J=13.5 Hz, 0.5H), 3.06 (d, J=13.6 Hz, 0.5H), 3.55 (dd, J=2.4, 11.9 Hz, 0.5H), 3.88 (dd, J=3.1, 10.2 Hz, 0.5H), 7.17-7.31 (m, 5H).

(Molecular Weight Measurement)

Theoretical ESI-MS value $C_{12}H_{15}NO_5$=253.26 Analytical value=252.23 (M-H)$^-$.

Example 12

Synthesis of 2-amino-4-benzyl-4-hydroxyglutaric acid; NO. 2

0.13 g (0.52 mmol) of 4-benzyl-4-hydroxy-2-ketoglutaric acid and 0.11 ml (1.0 mmol) of benzylamine were dissolved in 5 ml of methanol, to which 0.1 g of 5% palladium carbon (50% hydrous product) was added, for reaction under hydrogen atmosphere at ambient temperature and atmospheric pressure. Two days later, the catalyst was filtered off, and the reaction solution was concentrated to dryness, to obtain 0.03 g (0.12 mmol) of (2S,4S)/(2R,4R)-2-amino-4-benzyl-4-hydroxyglutaric acid and 0.06 g (0.24 mmol) of (2R,4S)/(2S, 4R)-2-amino-4-benzyl-4-hydroxyglutaric acid as a mixture.

Example 13

Synthesis of 4-hydroxy-4-(4-hydroxyphenylmethyl)-2-hydroxyiminoglutaric acid

To 10 ml of water in which were dissolved 3.18 g of potassium hydroxide, were added 1.0 g (5.55 mmol) of 4-hydroxyphenylpyruvic acid and 2.2 g (16.7 mmol) of oxalacetic acid, for reaction at ambient temperature for 72 hours (about pH 13 at the start of the reaction). Hydroxylamine hydrochloride salt of 1.54 g (22.2 mmol) was added to the reaction solution, for reaction at ambient temperature for 10 hours. The reaction solution was then adjusted to pH 2.6, using 6N hydrochloric acid, for extraction using ethyl acetate. The organic layer was rinsed with aqueous saturated sodium chloride, dried over anhydrous magnesium sulfate and concentrated to dryness, to obtain 0.7 g (2.47 mmol) of 4-hydroxy-4-(4-hydroxyphenylmethyl)-2-hydroxyiminoglutaric acid as a crude product. Further, the crude product was recrystallized in methanol and toluene, to obtain 0.22 g (0.78 mmol) of 4-hydroxy-4-(4-hydroxyphenylmethyl)-2-hydroxyiminoglutaric acid in crystal.

(NMR Measurement)

$^1$H NMR (DMSO-$d_6$) δ:2.67 (d, J=13.7 Hz, 1H), 2.89 (d, J=13.7 Hz, 1H), 2.95 (d, J=12.5 Hz, 1H), 2.99 (d, J=12.5 Hz, 1H), 6.59 (d, J=8.0 Hz, 2H), 6.97 (d, J=8.0 Hz, 2H), 9.11 (br s, 1H).

(Molecular Weight Measurement)

Theoretical ESI-MS value $C_{12}H_{13}NO_6$=283.24 Analytical value=281.93 (M-H)⁻.

Example 14

Synthesis of 4-hydroxy-4-(4-hydroxyphenylmethyl)-2-hydroxyiminoglutarate acid 0.06 g (0.21 mmol) of 4-hydroxy-4-(4-hydroxyphenylmethyl)-2-hydroxyiminoglutarate acid was dissolved in 2.5 ml of aqueous 28% ammonia, to which 0.04 g of 5% rhodium carbon was added for reaction at ambient temperature and a hydrogen pressure of 7.5 atmospheres. 14 hours later, the catalyst was filtered off, and the resulting solution was concentrated to dryness, to obtain a mixture of 0.044 g (0.145 mmol) of (2S,4S)/(2R,4R)-4-hydroxy-4-(4-hydroxyphenylmethyl)-2-aminoglutaric acid and 0.021 g (0.069 mmol) of (2S,4R)/(2R,4S)-4-hydroxy-4-(4-hydroxyphenylmethyl)-2-aminoglutaric acid.

$^1$H NMR (D$_2$O) δ: 1.89 (dd, J=11.9, 15.7 Hz, 0.68H), 2.06 (dd, J=10.2, 15.0 Hz, 0.32H), 2.30 (dd, J=3.3, 15.0 Hz, 0.32H), 2.51 (dd, J=2.4, 15.7 Hz, 0.68H), 2.70 (d, J=13.4 Hz, 0.68H), 2.83 (d, J=13.4 Hz, 0.32H), 2.90 (d, J=13.4 Hz, 0.32H), 2.96 (d, J=13.4 Hz, 0.68H), 3.52 (dd, J=2.4, 11.9 Hz, 0.68H), 3.84 (dd, J=3.3, 10.2 Hz, 0.32H), 6.71-6.77 (m, 2H), 7.02-7.08 (m, 2H).

(Molecular Weight Measurement)

Theoretical ESI-MS value $C_{12}H_{15}NO_6$=269.26 Analytical value=268.11 (M-H)⁻.

Example 15

Synthesis of 4-hydroxy-4-(3-indolylmethyl)-2-ketoglutaric acid; NO. 4

12.30 g (58.7 mmol; at a purity of 97.0% by weight) of indole pyruvic acid was added to and dissolved in 209 ml of water containing 2.45 g of sodium hydroxide dissolved therein. Over a period of two hours 47.61 g of an aqueous 25% by weight sodium hydroxide solution and a mixture of 25.85 g (293.5 mmol) of pyruvic acid and 25.85 g of water were added to the resulting solution under a nitrogen atmosphere at 35° C., while the reaction system was kept at pH 11.0. Subsequently, the reaction system was agitated for 14 hours. In this way, a reaction solution was obtained, which contained 4-hydroxy-4-(3-indolylmethyl)-2-ketoglutaric acid at a yield of 44.1% (vs. indolepyruvic acid). 3.60 g of 1N hydrochloric acid was added to the solution for neutralization (pH=6.91), to obtain 275 ml of a neutralized reaction solution.

168 ml of the thus obtained neutralized reaction solution was passed through a resin column (having a diameter of 4.8 cm) packed with 840 ml of a synthetic adsorbent (DIAION-SP207 manufactured by Mitsubishi Chemical Corporation). Then, pure water was passed through the column at a flow rate of 23.5 ml per minute, to collect 1.7 to 2.9 (L/L-R) to obtain 4-hydroxy-4-(3-indolylmethyl)-2-ketoglutaric acid at a high purity at a yield of 66.3%.

(NMR Spectrum)

$^1$H-NMR (400 MHz, D$_2$O): δ3.03 (d, 1H, J=14.6 Hz), 3.11 (d, 11, J=14.6 Hz), 3.21 (d, 1H, J=18.1 Hz), 3.40 (d, 1H, J=18.1 Hz), 7.06-7.15 (m, 3H), 7.39 (d, 1H, J=7.8 Hz), 7.66 (d, 1H, J=7.8 Hz). $^{13}$C-NMR (400 MHz, D$_2$O): δ35.43, 47.91, 77.28, 109.49, 112.05, 119.44, 119.67, 121.91, 125.42, 128.41, 136.21, 169.78, 181.43, 203.58.

(Mass Analysis)

Theoretical ESI-MS value $C_{14}H_{13}NO_6$=291.07 Analytical value=290.02 (M-H)⁻.

Example 16

Synthesis of 4-hydroxy-4-(3-indolylmethyl)-2-hydroxyiminoglutaric acid; NO. 2

After 1.0 g (4.92 mmol) of indole-3-pyruvic acid was added to and dissolved in 10 ml of aqueous saturated sodium carbonate solution, the resulting solution was adjusted to pH 12.55 using aqueous 25% sodium hydroxide solution. After 1.3 g (14.8 mmol) of pyruvic acid was added, the resulting solution was adjusted to pH 12.6 using aqueous 25% sodium hydroxide solution, for reaction at ambient temperature for 2 hours, to obtain a reaction solution containing 4-hydroxy-4-(3-indolylmethyl)-2-ketoglutaric acid. 1.37 g (19.7 mmol) of hydroxylamine hydrochloride salt was added to the reaction solution, while the reaction solution was adjusted to a pH value around neutrality using aqueous 25% sodium hydroxide solution, and stirred at ambient temperature for 4 hours. Using conc. hydrochloric acid, the reaction solution was adjusted to an acidic pH value, to extract the organic matter in ethyl acetate. The organic layer was rinsed with aqueous saturated sodium chloride, dried over anhydrous magnesium sulfate and subsequently concentrated, to obtain the residue. The residue was recrystallized in aqueous 28% ammonia and ethanol, to obtain 0.52 g of 4-hydroxy-4-(3-indolylmethyl)-2-hydroxyiminoglutaric acid (1.5 mmol; a yield, 31% vs. indole-3-pyruvic acid) in crystal form.

(NMR Spectrum)

$^1$HNMR (DMSO-$d_6$) δ: 2.66 (s, 2H), 2.89 (d, J=14.4 Hz, 1H), 3.04 (d, J=14.4 Hz, 1H), 6.89-6.94 (m, 1H), 6.97-7.03 (m, 1H), 7.11 (d, J=2.8 Hz, 1H), 7.27 (d, J=7.8 Hz, 1H), 7.53 (d, J=7.8 Hz, 1H), 10.71 (br s, 1H).

(Mass Analysis)

Theoretical ESI-MS value $C_{14}H_{14}N_2O_6$=306.28 Analytical value=305.17 (M-H)$^-$.

Example 17

Synthesis of 4-hydroxy-4-(3-indolylmethyl)-2-hydroxyiminoglutaric acid; NO. 3

After 10.0 g (49.2 mmol) of indole-3-pyruvic acid was added to and dissolved in 98 ml of aqueous saturated sodium carbonate solution, the resulting solution was adjusted to pH 12.4 using aqueous 25% sodium hydroxide solution. After 16.3 g (147.6 mmol) of sodium pyruvate was added for reaction at ambient temperature for 2 hours, a reaction solution containing 4-hydroxy-4-(3-indolylmethyl)-2-ketoglutaric acid was obtained. 13.7 g (197 mmol) of hydroxylamine hydrochloride salt was added to the reaction solution while the reaction solution was adjusted to a pH value around neutrality using aqueous 25% sodium hydroxide solution, and agitated at ambient temperature for 4 hours. Using conc. hydrochloric acid, the reaction solution was adjusted to an acidic pH value, to extract the organic matter in ethyl acetate. The organic layer was rinsed with aqueous saturated sodium chloride, dried over anhydrous magnesium sulfate and subsequently concentrated, to obtain the residue. The residue was recrystallized in aqueous 28% ammonia and ethanol, to obtain 5.51 g of 4-hydroxy-4-(3-indolylmethyl)-2-hydroxyiminoglutaric acid (16.2 mmol; a yield of 32% vs. indole-3-pyruvic acid) in crystal form.

Example 18

After 1.0 g (4.92 mmol) of indole-3-pyruvic acid was added to and dissolved in 10 ml of aqueous saturated sodium carbonate solution in the same manner as in Example 16, the resulting solution was adjusted to pH 12.7 using aqueous 25% sodium hydroxide solution. After 1.3 g (14.8 mmol) of pyruvic acid was added, the resulting solution was adjusted to pH 10.0 using aqueous 25% sodium hydroxide solution, for reaction at ambient temperature for 6 hours. 1.37 g (19.7 mmol) of hydroxylamine hydrochloride salt was added to the reaction solution while the reaction solution was adjusted to a pH value around neutrality using aqueous 25% sodium hydroxide solution, and stirred at ambient temperature for 13 hours. Using conc. hydrochloric acid, the reaction solution was adjusted to an acidic pH value, to extract the organic matter in ethyl acetate. The organic layer was rinsed with aqueous saturated sodium chloride, dried over anhydrous magnesium sulfate and subsequently concentrated, to obtain the residue. The residue was analyzed by HPLC, by which it was shown that 4-hydroxy-4-(3-indolylmethyl)-2-hydroxyiminoglutaric acid was generated at a yield of about 14%.

Example 19

Synthesis of 4-hydroxy-4-(3-indolylmethyl)-2-hydroxyiminoglutaric acid; NO. 4

73.8 g (352 mmol) of indole-3-pyruvic acid was added to and dissolved in 917 g of aqueous 1.6 wt % sodium hydroxide solution. The resulting solution was adjusted to 35° C., to which 310.2 g (1761 mmol) of aqueous 50% pyruvic acid solution was added dropwise over 2 hours, while the reaction solution was retained at pH 11.1 using aqueous 30% sodium hydroxide solution. After reaction for another 4.5 hours, a reaction solution containing 4-hydroxy-4-(3-indolylmethyl)-2-ketoglutaric acid was obtained. 367.2 g (2114 mmol) of aqueous 40% hydroxylamine hydrochloride salt solution was added to the reaction solution while the reaction solution was kept at pH 7 using aqueous 30% sodium hydroxide solution, and stirred at 5° C. for 17.5 hours. Using conc. hydrochloric acid, the reaction solution was adjusted to pH 2, to extract the organic matter in ethyl acetate. The organic layer was rinsed with aqueous saturated sodium chloride and concentrated, to obtain the residue. The residue was recrystallized in 60 ml of aqueous 28% ammonia and 1350 ml of 2-propanol, to obtain 43.4 g of the diammonium salt of 4-hydroxy-4-(3-indolylmethyl)-2-hydroxyiminoglutaric acid (142 mmol; a yield of 40% vs. indole-3-pyruvic acid) in crystal form.

Example 20

Production of (R)-(+)-1-phenylethylamine salt of (4S)-4-hydroxy-4-(3-indolylmethyl)-2-hydroxyiminoglutaric acid After 44.7 g (0.131 mol) of the ammonium salt of 4-hydroxy-4-(3-indolylmethyl)-2-hydroxyiminoglutaric acid was dissolved in 500 ml of water at 25° C., the resulting aqueous solution was adjusted to pH 2 using 25.5 g of 36% hydrochloric acid. The acidic solution was extracted in 1300 ml of ethyl acetate, and the resulting ethyl acetate solution was rinsed with 200 ml of aqueous saturated sodium chloride solution. 500 ml of an aqueous sodium carbonate solution (13.9 g (0.131 mole) of sodium carbonate) was added to the resulting ethyl acetate solution for agitation, to separate the aqueous alkali solution from ethyl acetate. 23.1 g of 36% hydrochloric acid was added to the resulting aqueous alkali solution, to adjust the solution to pH 2. 6.99 g (57.6 mmol) of (R)-(+)-1-phenylethylamine was added dropwise to the resulting aqueous acidic solution and the solution stirred at 25° C. for one hour. The resulting crystal was filtered and dried under reduced pressure, to obtain 21.8 g (47.8 mmol) of the (R)-(+)-1-phenylethylamine salt of (4S)-4-hydroxy-4-(3-indolylmethyl)-2-hydroxyiminoglutaric acid. (Yield, 72.7%; optical purity, 87.4%.)

$^1$H-NMR (400 MHz, DMSO-$d_6$) σ: 1.48 (d, 3H, J=6.8 Hz), 2.63 (d, 1H, J=14.0 Hz), 2.70 (d, 1H, J=14.0 Hz), 2.90 (d, 1H, J=14.1 Hz), 3.06 (d, 1H, J=14.1 Hz), 4.40 (q, 1H, J=6.8 Hz), 6.91-7.54 (m, 10H).

Example 21

Production of (S)-(−)-1-phenylethylamine salt of (4R)-4-hydroxy-4-(3-indolylmethyl)-2-hydroxyiminoglutaric acid (S)-(−)-1-phenylethylamine of 7.12 g (58.7 mmol) was added dropwise to the solution obtained in Example 20 after the crystal was filtered off, and the mixtured stirred at 25° C. for one hour. The resulting crystal was filtered off and dried under reduced pressure, to obtain of 23.8 g (53.3 mol) the (S)-(−)-1-phenylethylamine salt of (4R)-4-hydroxy-4-(3-indolylmethyl)-2-hydroxyiminoglutaric acid. (Yield, 81.1%; optical purity, 92.1%.)

Example 22

Production of the ammonium salt of (4S)-4-hydroxy-4-(3-indolylmethyl)-2-hydroxyiminoglutaric acid 200 ml of water and 18.5 g of aqueous 28% ammonia were added to 21.8 g (51.0 mmol) of the (R)-(+)-1-phenylethylamine salt of (4S)-4-hydroxy-4-(3-indolylmethyl)-2-hydroxyiminoglutaric acid at 25° C. so as to dissolve the salt, followed by further addition of 200 ml of toluene and stirring. The aqueous layer obtained by the partition of the resulting layers was heated to 60° C. To the resulting aqueous solution was added dropwise 900 ml of 2-propanol over 2 hours. After the aqueous 2-propanol solution was cooled to 10° C. over 5 hours, the solution was stirred at 10° C. for 10 hours. The resulting crystal was filtered and dried under reduced pressure, to obtain 14.75 g of the ammonium salt of (4S)-4-hydroxy-4-(3-indolylmethyl)-2-hydroxyiminoglutaric acid. (Yield, 85.1%; optical purity, 99.0%.)

Melting point; 205° C. (decomposed) Specific rotation $[\alpha]^{20}{}_D$+13.4 (c=1.00, H$_2$O).

Example 23

Production of the ammonium salt of (4R)-4-hydroxy-4-(3-indolylmethyl)-2-hydroxyiminoglutaric acid In the same manner as in the Example described above, 16.2 g the ammonium salt of (4R)-4-hydroxy-4-(3-indolylmethyl)-2-hydroxyiminoglutaric acid was recovered of 23.8 g (53.3 mmol) of from the (S)-(−)-1-phenylethylamine salt of (4R)-4-hydroxy-4-(3-indolylmethyl)-2-hydroxyiminoglutaric acid. (Yield, 89.3%; optical purity, 99.9%.)

Specific rotation $[\alpha]^{20}{}_D$−13.6 (c=1.00, H$_2$O).

Example 24

Production of (2S,4S) monatin 4.5 g (13.1 mmol) of the ammonium salt of (4S)-4-hydroxy-4-(3-indolylmethyl)-2-hydroxyiminoglutaric acid was dissolved in 100 ml of aqueous 28% ammonia, followed by addition of 3.4 g of 5% rhodium carbon (50% hydrous product), for reaction at ambient temperature and a hydrogen pressure of 10 atmospheres (1 MPa). After 24 hours, the catalyst was filtered off. The filtrate was concentrated. 40 ml of aqueous 90% ethanol was added to the concentrate, for stirring at 25° C. for 1.5 hours. The deposited crude crystal was filtered. 40 ml of aqueous 90% ethanol was added to the crude crystal, and stirred at 25° C. for 1.5 hours. The deposited purified crystal was filtered off and dried under reduced pressure, to obtain 0.57 g (1.84 mmol) of the ammonium salt of (2S,4S) monatin. (Yield, 14.1%; optical purity, 99.5%.)

$^1$HNMR (400 MHz, D$_2$O) δ: 2.06 (dd, J=11.8, 15.3 Hz, 1H), 2.67 (dd, J=2.0, 15.2 Hz, 1H), 3.08 (d, J=14.4 Hz, 1H), 3.28 (d, J=14.4 Hz, 1H) 3.63 (dd, J=2.2, 12.2 Hz, 1H), 7.12-7.16 (m, 1H), 7.20-7.24 (m, 2H), 7.48-7.49 (m, 1H), 7.71-7.73 (m, 1H). Theoretical ESI-MS value C$_{14}$H$_{16}$N$_2$O$_5$=292.29 Analytical value=291.28 (MH$^-$).

Example 25

Production of ammonium salt of (2S,4S) monatin 14.0 g (41.1 mmol) of the ammonium salt of (4S)-4-hydroxy-4-(3-indolylmethyl)-2-hydroxyiminoglutaric acid was dissolved in 120 ml of aqueous 28% ammonia, followed by addition of 7.38 g of 5% rhodium carbon (50% hydrous product), for reaction at 25° C. and a hydrogen pressure of 1 MPa. After 24 hours, the catalyst was filtered off. The filtrate was concentrated. 110 ml of aqueous 88% ethanol was added to 17.68 g of the concentrate, for stirring at 25° C. for 19 hours. The resulting crude crystal was filtered off and dissolved in 15 ml of water, followed by addition of 100 ml of ethanol. After stirring at 25° C. for 1.5 hours, the deposited purified crystals was filtered and dried under reduced pressure, to obtain 4.94 g (16.0 mmol) of the ammonium salt of (2S,4S) monatin. (Yield, 39.2%; optical purity, 99.9%.)

Example 26

Production of free form of (2S,4S) monatin 2.22 g (7.18 mmol) of the ammonium salt of (2S,4S) monatin obtained in the above Example was dissolved in a mixed solvent of 4.5 ml of water and 4.2 ml (71.8 mmol) of acetic acid, followed by dropwise addition of 50 ml of ethanol to the resulting solution at 25° C. over about 3 hours. After another 0.5-hr stirring, the resulting crystal was filtered and dried under reduced pressure, to obtain 1.93 g (6.62 mmol) of (2S,4S) monatin of. (Yield, 92.2%; the ammonium content, 0.19 wt %.)

Comparative Example 1

Using cinchonidine in place of the optically active amine used in Example 20, the same procedures were carried out. The optical purity of the resulting crystal was 0%.

Comparative Example 2

L-Lysine was used in place of the optically active amine used in Example 20. However, no crystal was obtained.

Comparative Example 3

L-Arginine was used in place of the optically active amine used in Example 20. However, no crystal was obtained.

INDUSTRIAL APPLICABILITY

In accordance with the invention, glutamic acid compounds typically including monatin useful as sweetener or an intermediate for producing pharmaceutical products can be efficiently produced industrially. In accordance with the invention, further, optically active monatin can be efficiently produced industrially.

The present application is based on Japanese application No. 2001-396300 (filed Dec. 27, 2001), Japanese application No. 2002-149069 (filed May 23, 2002), Japanese application No. 2002-149078 (filed May 23, 2002), and Japanese application No. 2002-182032, filed Jun. 21, 2002, all of which are incorporated herein by reference.

The invention claimed is:

1. A compound represented by formula (4'), or a salt thereof:

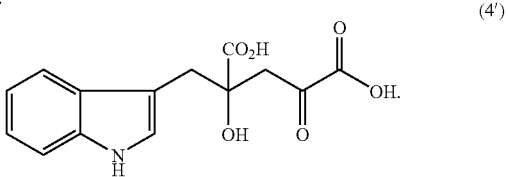

(4')

2. The compound of claim 1, which is a sodium salt, potassium salt, magnesium salt, ammonium salt or dicyclohexylammonium salt.

* * * * *